US008986529B2

(12) United States Patent
Santiago et al.

(10) Patent No.: US 8,986,529 B2
(45) Date of Patent: Mar. 24, 2015

(54) ISOTACHOPHORESIS HAVING INTERACTING ANIONIC AND CATIONIC SHOCK WAVES

(75) Inventors: Juan G. Santiago, Stanford, CA (US); Robert D. Chambers, Enfield, NH (US); Supreet Singh Bahga, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 13/199,895

(22) Filed: Sep. 12, 2011

(65) Prior Publication Data

US 2012/0061242 A1 Mar. 15, 2012

Related U.S. Application Data

(60) Provisional application No. 61/403,275, filed on Sep. 13, 2010.

(51) Int. Cl.
*G01N 27/447* (2006.01)
*B01D 57/02* (2006.01)

(52) U.S. Cl.
CPC ........ *G01N 27/447* (2013.01); *G01N 27/44717* (2013.01); *B01D 57/02* (2013.01); *G01N 27/44721* (2013.01)
USPC ............................. 204/549; 204/645; 204/548

(58) Field of Classification Search
CPC .......... G01N 27/447; G01N 27/44717; G01N 27/44712; B01D 57/02
USPC .................................................. 204/549, 645
See application file for complete search history.

(56) References Cited

U.S. PATENT DOCUMENTS 3,869,365 A   3/1975 Sunden
3,948,753 A   4/1976 Arlinger
(Continued)

FOREIGN PATENT DOCUMENTS

EP   1742057    1/2007
EP   2340122 A1  7/2011

OTHER PUBLICATIONS

Persat, et al., Anal. Chem. 2009, 81, 9507-9511.*
(Continued)

*Primary Examiner* — Luan Van
*Assistant Examiner* — Steven Rosenwald
(74) *Attorney, Agent, or Firm* — Lumen Patent Firm

(57) ABSTRACT

Improved electrophoretic analysis is provided by interaction of anionic and cationic isotachophoresis (ITP) shock waves that propagate toward each other, and analysis of the resulting interaction zones. These shock wave interactions can provide qualitatively different capabilities from conventional ITP methods. Shock wave interaction can enable a single assay to identify analyte and quantify its concentration via isotachophoretic focusing followed by separation of the concentrated analytes via electrophoresis, without any mid-assay alteration of the externally imposed experimental conditions (i.e., no switching, valve operation, etc. during the measurement). As another example, shock wave interaction can enable a single assay to provide coupled ITP processes with different electrolyte concentrations (as in cascade-ITP) in a single simple system (again, without any mid-assay alteration of the externally imposed experimental conditions).

12 Claims, 13 Drawing Sheets

(56) References Cited

U.S. PATENT DOCUMENTS

| | | | |
|---|---|---|---|
| 4,897,169 A | 1/1990 | Bier et al. |
| 5,447,612 A | 9/1995 | Bier et al. |
| 5,464,515 A | 11/1995 | Bellon |
| 5,817,225 A | 10/1998 | Hinton |
| 5,939,291 A | 8/1999 | Loewy et al. |
| 6,685,813 B2 | 2/2004 | Williams et al. |
| 6,780,584 B1 | 8/2004 | Edman et al. |
| 6,818,113 B2 | 11/2004 | Williams et al. |
| 6,934,836 B2 | 8/2005 | Strand et al. |
| 7,214,299 B2 | 5/2007 | Armstrong |
| 7,223,325 B2 | 5/2007 | Landers et al. |
| 7,316,771 B2 | 1/2008 | Weber |
| 7,371,533 B2 | 5/2008 | Slater et al. |
| 7,399,394 B2 | 7/2008 | Weber |
| 7,473,551 B2 | 1/2009 | Warthoe |
| 7,494,577 B2 | 2/2009 | Williams et al. |
| 7,517,442 B1 | 4/2009 | Champagne |
| 7,635,563 B2 | 12/2009 | Horvitz et al. |
| 7,951,278 B2 | 5/2011 | Santiago et al. |
| 8,017,408 B2 | 9/2011 | Meinhart et al. |
| 8,021,531 B2 | 9/2011 | Park et al. |
| 8,133,371 B2 | 3/2012 | Marziali et al. |
| 8,277,628 B2 | 10/2012 | Ronaghi et al. |
| 8,394,251 B2 | 3/2013 | Santiago et al. |
| 2004/0031683 A1 | 2/2004 | Eipel et al. |
| 2005/0121324 A1 | 6/2005 | Park et al. |
| 2005/0133370 A1 | 6/2005 | Park et al. |
| 2005/0170362 A1 | 8/2005 | Wada et al. |
| 2006/0042948 A1 | 3/2006 | Santiago et al. |
| 2006/0078998 A1 | 4/2006 | Puskas et al. |
| 2008/0020386 A1 | 1/2008 | Chen et al. |
| 2008/0021674 A1 | 1/2008 | Puskas |
| 2008/0156080 A1 | 7/2008 | Balgley |
| 2008/0166770 A1 | 7/2008 | Morita et al. |
| 2009/0178929 A1 | 7/2009 | Broer et al. |
| 2010/0116657 A1 | 5/2010 | Fiering et al. |
| 2010/0224494 A1* | 9/2010 | Chambers et al. ............ 204/549 |
| 2010/0261612 A1 | 10/2010 | Young |
| 2010/0270157 A1 | 10/2010 | Kurosawa et al. |
| 2010/0323913 A1 | 12/2010 | Young et al. |
| 2011/0024296 A1 | 2/2011 | Park et al. |
| 2011/0036718 A1 | 2/2011 | Jung et al. |
| 2011/0174624 A1 | 7/2011 | Weber |
| 2011/0220499 A1 | 9/2011 | Chambers et al. |
| 2011/0297546 A1 | 12/2011 | Schoch |
| 2012/0061242 A1 | 3/2012 | Santiago et al. |
| 2012/0152746 A1 | 6/2012 | Santiago et al. |
| 2012/0160689 A1 | 6/2012 | Utz et al. |
| 2012/0175258 A1 | 7/2012 | Mariella, Jr. |

OTHER PUBLICATIONS

Persat, et al., Anal. Chem. 2009, 81, 9507-9511, supporting materials.*

Oshurkova et al., Russ. J. Electrochem., 40(5), 2004, pp. 583-587.*

Křivánková et al., J. Chromatogr. B, 689, 1997, 13-34.*

Boček et al., J. Chromatograph., 156, 1978, 323-326.*

Oshurkova et al. (Russ. Chem. Rev. 62(8) 729-742, 1993).*

Prest et al., "Bidirectional isotachophoresis on a planar chip with integrated conductivity detection", 2002, pp. 1413-1419, Analyst v127.

Oshurkova et al., "Coulophoretic titration", 1975, p. 316-319, Translated from Doklady Akademii Nauk SSSR v227n6.

Gohring, et al. The scaffold/matrix attachment region binding protein hnRNP-U (SAF-A) is directly bound to chromosomal DNA in vivo: a chemical cross-linking study. Biochemistry. Jul. 8, 1997;36(27):8276-83.

Morio, et al. Quantitative analysis of trifluoroacetate in the urine and blood by isotachophoresis. Anesthesiology. Jul. 1980;53(1):56-9.

US 7,247,224, 07/2007, Weber (withdrawn)

* cited by examiner

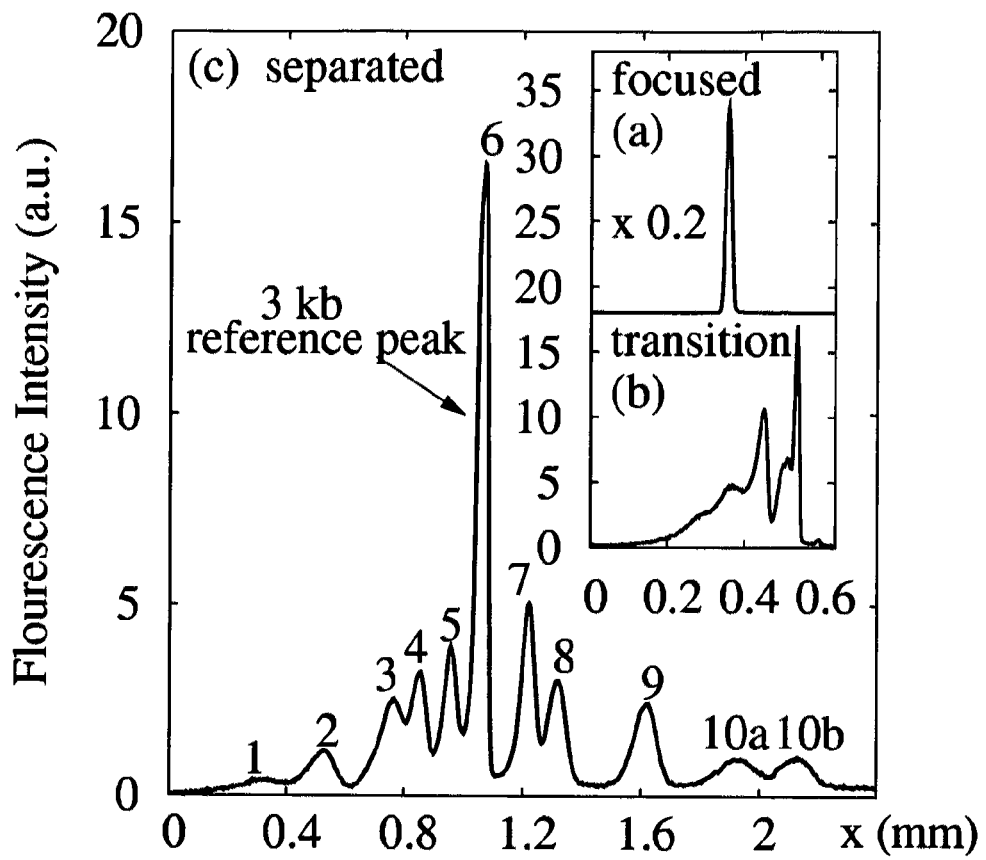
Figs. 6a,b,c
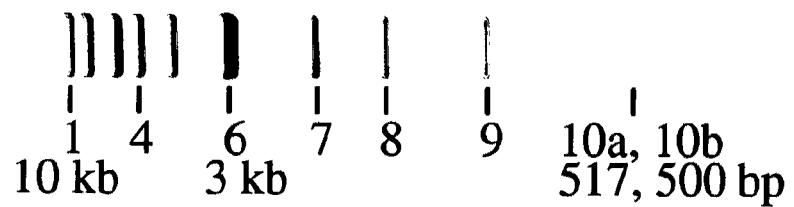
Fig. 6d

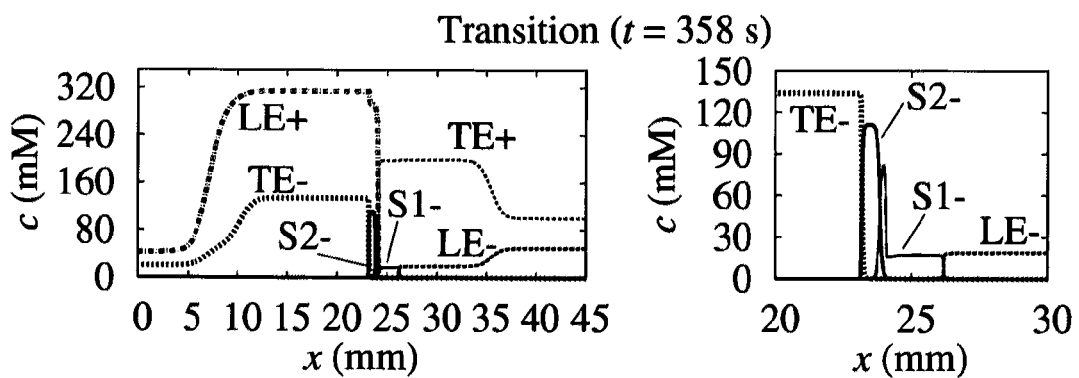
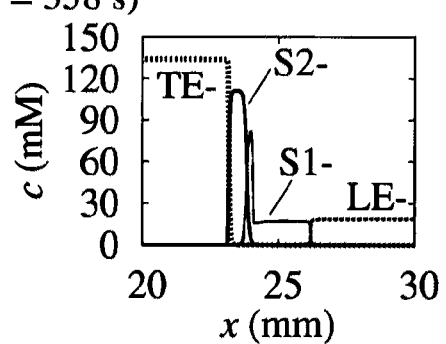
Fig. 8e
Fig. 8f
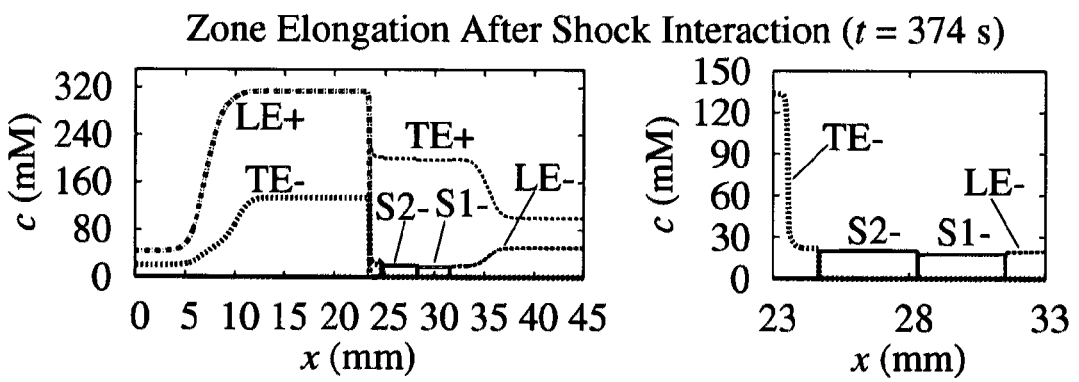
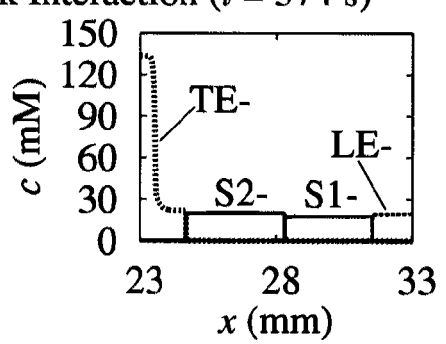
Fig. 8g
Fig. 8h

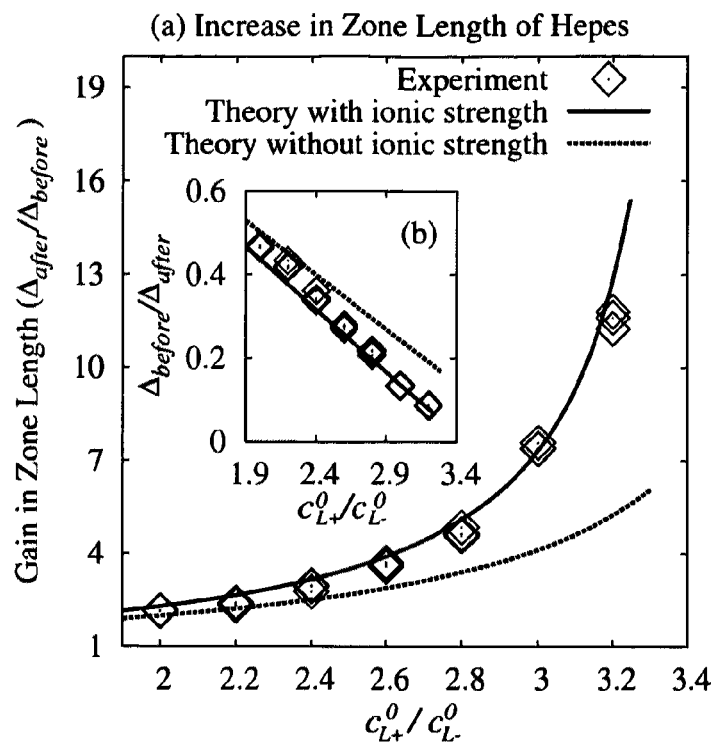
Figs. 10a-b
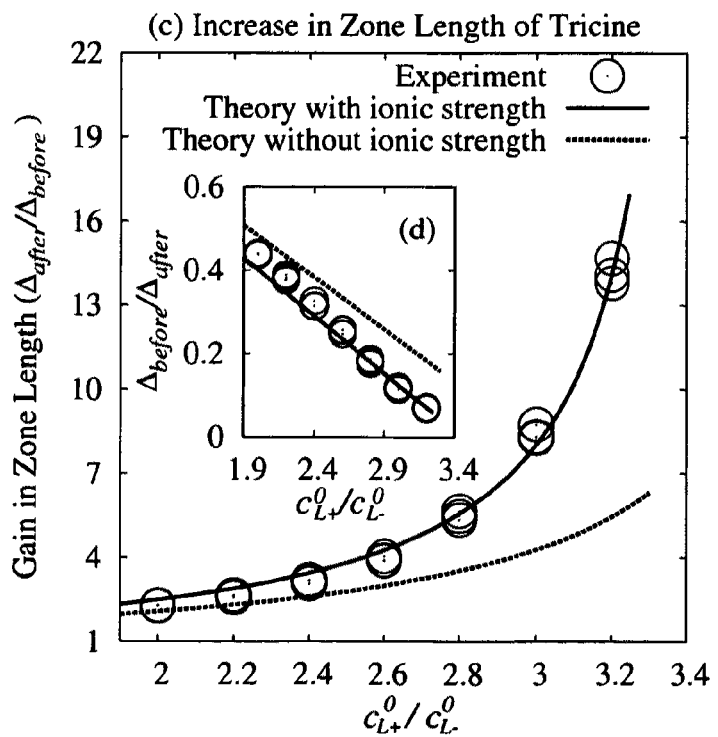
Figs. 10c-d

ISOTACHOPHORESIS HAVING INTERACTING ANIONIC AND CATIONIC SHOCK WAVES

CROSS REFERENCE TO RELATED APPLICATIONS

This application claims the benefit of U.S. provisional patent application 61/403,275, filed on Sep. 13, 2010, entitled "Bi-directional anionic-cationic isotachophoresis", and hereby incorporated by reference in its entirety.

GOVERNMENT SPONSORSHIP

This invention was made with Government support under contract N66001-09-C-2082 awarded by the SPA WAR SYS CEN. The Government has certain rights in this invention.

FIELD OF THE INVENTION

This invention relates to isotachophoresis.

BACKGROUND

Isotachophoresis (ITP) is a preconcentration and separation technique which leverages electrolytes with different electrophoretic mobility to focus (and in some cases, separate) ionic analytes into distinct zones. In ITP, analytes simultaneously focus and separate between high effective mobility leading electrolyte (LE) ions and low effective mobility trailing electrolyte (TE) ions. The balance of electromigration and diffusion at the zone boundaries in ITP results in sharp moving boundaries which can be described as ion concentration shock waves. It is convenient to refer to such boundaries as "shock waves", "shocks" or "ITP shocks" for brevity. We note that "shock wave" is a generic term which has been used in the literature to describe self-sharpening discontinuities due to non-linear advection flux in a variety of physical processes, such as fluid flow, chromatography, ITP, sedimentation boundaries, and automotive traffic flow.

Typically, ITP experiments are performed separately for focusing anions or cations in respectively anionic and cationic ITP. However, anionic and cationic ITP can also be performed simultaneously in a single channel. The latter approach, called bidirectional ITP, has been used to provide simultaneous separation of anions and cations with ITP. An article by Prest et al. (*Bidirectional isotachophoresis on a planar chip with integrated conductivity detection*, Analyst, 2002, 127, pp. 1413-1419) is an example of this approach.

SUMMARY

The present approach is based on interaction of anionic and cationic ITP shock waves that propagate toward each other, and analysis of the resulting interaction zones. These shock wave interactions can provide qualitatively different capabilities from conventional ITP methods. For example, as described in greater detail below, shock wave interaction can enable a single assay to provide analyte identity and its concentration via isotachophoretic focusing followed by separation of the concentrated analytes via electrophoresis, without any mid-assay alteration of the externally imposed experimental conditions (i.e., no switching, valve operation, etc. during the measurement). As another example, shock wave interaction can enable a single assay to provide coupled ITP processes with different electrolyte concentrations, as in cascade-ITP, in a single simple system (again, without any mid-assay alteration of the externally imposed experimental conditions).

In cases where ITP shock wave interaction causes focused analytes to separate, it is convenient to refer to this as a focusing to separation mode. In cases where ITP shock wave interaction causes focused analytes to remain focused (usually with different properties such as zone length), it is convenient to refer to this as a focusing to focusing mode.

Shock wave interaction ITP has the following advantages, regardless of the mode of operation:
1) Small initial concentration of sample is required due to the preconcentration step.
2) Small initial total amount of sample is required due to both the preconcentration step and the relatively small dimensions of the reservoir and microchannel.
3) Automated transition from focusing to separation or focusing mode, as no intermediate steps are involved. For example, once initial loading is complete, there are no manual steps required such as buffer exchange, voltage change, or sample loading.
4) The process can be easily integrated in conventional capillary electrophoresis (CE) equipment, including single channel systems, as no intermediate step is involved between focusing and separation steps.
5) The initial separation step can also be used as a purification step to selectively focus analytes of choice. For example, an optimal choice of TE can selectively focus DNA and reject contaminants such as proteins (typical contaminants in sample preparation).

In addition to the above mentioned advantages, the focusing to separation mode has at least the following advantages:
a) Initial focusing of analytes in a sharp peak increases the detection sensitivity of separation.
b) Separation initiates as soon as anionic and cationic shocks interact. This reduces the assay time, compared to transient ITP (t-ITP), where LE ions injected behind TE take a while to overtake focused analytes.
c) Fast transition from focusing to separation minimizes dispersion and increases separation resolution due to smaller conductivity gradients and associated non-uniform electro-osmotic flow. This is in contrast to transient ITP (t-ITP_) where a prolonged transition phase causes significant dispersion which leads to a lower separation resolution.

The focusing to focusing mode has at least the following additional advantages:
d) Requires only a single channel to couple two ITP focusing steps with different concentrations of LE, as in normal cascade-ITP. Creating a step change in LE concentration otherwise requires valves or T-shaped channel geometry.
e) Operation of focusing to focusing ITP is simple in comparison to normal cascade-ITP which requires multiple electrodes and switching voltages between channels with high concentration and low concentration LE.

In the absence of net bulk flow, the cationic and anionic shocks will move in opposite directions and approach each other. However, bulk liquid flow (e.g., due to either significant electroosmotic flow or applied pressure-driven flow) in the channel can change the net motion of these shocks relative to the frame of reference of the laboratory. For example, a sufficiently strong bulk flow from the positive to the negative electrode can cause both cationic and anionic shocks to move toward the negative electrode. Nevertheless, our interest here includes shock interactions and the results of these interactions, and so we are interested in all cases where at least one cationic and at least one anionic shock approach each other.

A method according to an embodiment of the invention includes the following steps. 1) Establishing anionic isotachophoresis (ITP) in a channel. The anionic ITP has one or more anionic ITP shock waves between an anionic leading electrolyte ion (LE−) and an anionic trailing electrolyte ion (TE−). 2) Establishing cationic ITP simultaneously in the same channel. The cationic ITP has one or more cationic ITP shock waves between a cationic leading electrolyte ion (LE+) and a cationic trailing electrolyte ion (TE+). The anionic and cationic ITP shock waves propagate toward each other in the channel and interact when they meet. As a result of this shock wave interaction, one or more interaction regions is created. 3) Analyzing at least one of the interaction regions to determine physicochemical properties of ions and/or interaction regions in the channel. These determined properties can be provided as an output of a measurement system and/or provided as an input for further processing to a downstream analysis and/or synthesis system.

Typically, isotachophoretic focusing of one or more analytes occurs in a selected shock wave of the anionic and cationic ITP shock waves, prior to the shock wave interaction. Electrophoretic separation of the one or more analytes can occur in at least one of the interaction regions after the shock wave interaction. This is an example of the focusing to separation mode, and is described in greater detail below in connection with FIGS. 1a-c. Isotachophoretic focusing of the one or more analytes can occur in at least one of the interaction regions after the shock wave interaction. This is an example of the focusing to focusing mode, and is described in greater detail below in connection with FIGS. 7a-c. Mixed modes are also possible, where some analytes experience focusing to focusing, and other analytes experience focusing to separation. It is also possible for analytes to focus in multiple selected ITP shock waves prior to the shock wave interaction.

In the focusing to focusing mode, one possible outcome is that ITP zone lengths of analytes in at least one of the interaction regions differ from ITP zone lengths of the analytes prior to the shock wave interaction. Preferably, the ITP zone length increases as a result of ITP shock wave interaction because that leads to an increase in measurement sensitivity.

Typically, the interaction region (or regions) formed by ITP shock wave interaction have new compositions, relative to the ITP zones prior to shock wave interaction. More specifically, if the anionic ITP has two or more anionic ITP zones prior to the shock wave interaction, and the cationic ITP has two or more cationic ITP zones prior to the shock wave interaction, then the interaction regions typically have compositions that are distinct from compositions of any of the anionic and cationic ITP zones.

Practice of the invention does not depend critically on the physicochemical property or properties that are measured. Suitable properties include, but are not limited to: conductivity, ionic strength, ionization state, species identity, pH, absorption spectra, emission spectra, temperature, concentration, effective mobility, electrophoretic mobility, degree of ionization, and acid dissociation constants.

This approach can be extended from analysis to any combination of analysis and synthesis/extraction. For example, one or more of the interaction regions can be extracted from the channel for use and/or further analysis. Similarly, the preceding method can be employed on a sample including analytes. Suitable analytes include, but are not limited to: biological analytes, chemical analytes, biochemical analytes, DNA, DNA fragments, RNA, RNA fragments, proteins, protein fragments, polypeptides and amino acids.

Selective preconcentration can be employed. For example, selective isotachophoretic focusing of a selected group of the analytes can occur in a selected shock wave of the anionic and cationic ITP shock waves. More specifically, if the analytes include one or more species of interest and one or more contaminant species, the selected group of the analytes preferably includes the one or more species of interest and preferably does not include the one or more contaminant species. For example, the species of interest could include DNA species, and the contaminant species could be proteins, which are often present in DNA samples and often need to be removed from DNA assays.

BRIEF DESCRIPTION OF THE DRAWINGS

FIGS. 6a-d show experimental DNA separation results from the protocol of FIGS. 5a-e.

FIGS. 8a-h show simulation results relating to the focusing to focusing mode.

FIGS. 10a-d show experimental results relating to increased ITP zone length provided by the focusing to focusing mode.

DETAILED DESCRIPTION

Figure 1A:
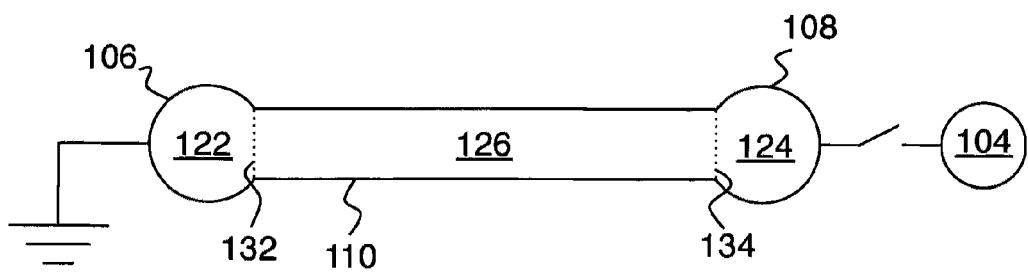
FIGS. 1a-c show operation of an ITP focusing to separation mode of embodiments of the invention.

The following description provides details relating to the two modes described above (i.e., focusing to separation, and focusing to focusing). For both modes, experimental and theoretical results are given. The focusing to separation mode will be considered first, followed by the focusing to focusing mode.

A) Focusing to Separation Mode

A1) Introduction

We view shock interaction in bidirectional ITP as an important process as it can lead to fundamental modification of the electrophoretic conditions. For example, shock interaction can initiate changes in counter-ion species, concentration of co-ion species, local pH (e.g., changing effective mobility), and species zone order. We here submit that shock interactions in bidirectional ITP can be used to initiate either modified ITP modes or electrophoresis modes. In this section, we demonstrate a bidirectional ITP experiment where shock interaction triggers a transformation from ITP preconcentration to electrophoretic separation. Traditional ITP buffer systems use only two co-ionic species (leading and trailing) and a single counter-ionic species. Here, our bidirectional experiments require four species (i.e., two oppositely-charged pairs of leading and trailing ions) which we term LE+, LE−, TE+, and TE−. Here, LE and TE again denote the leading and the trailing electrolyte ions, respectively, and + and − correspond to cations and anions, respectively. We explore the case of anionic analytes initially focused between TE– and LE–. Before the anionic and cationic ITP shocks meet, the counter-ion of the focused analyte zones is LE+. After these shocks meet, TE+ replaces LE+ as the counter-ion for analyte zones. This changes the pH such that ITP focusing conditions for analyte ions no longer hold and consequently analytes begin to separate electrophoretically. The method negates the need for deactivating power during the experiment or manual buffer exchanges as in conventional transient ITP (t-ITP) experiments.

We begin by describing the principle of coupling ITP preconcentration and electrophoretic separation using bidirectional ITP with converging anionic and cationic ITP shock waves. We discuss choices of electrolyte chemistries appropriate for coupling ITP focusing and electrophoretic separation. We then present simulations to illustrate the technique and verify our choice of electrolyte chemistry. We confirm these simulations by experimental visualization of interacting anionic and cationic ITP shocks. Using simulations, we then compare the separation resolution of bidirectional ITP and t-ITP. Lastly, using our technique we experimentally demonstrate coupled ITP preconcentration and high resolution separation of a 1 kbp ds-DNA ladder.

A2) Theory

A2.1) Concept of Initiating Electrophoresis Via ITP Shock Interaction

In ITP, analyte ions focus only if their charge has the same sign as respective LE and TE ions. Two other requirements for focusing analyte ions are that analyte ions should have higher effective mobility ($\mu$) than TE ions in both TE and analyte zones, $$|\mu_{a,T}|>|\mu_{te,T}|, |\mu_{a,A}|>|\mu_{te,A}|, \quad (1)$$

and that the effective mobility of analyte ions should be smaller than that of LE ions in both LE and analyte zones, $$|\mu_{a,L}|<|\mu le,L|, |\mu_{a,A}|<|\mu_{le,A}|. \quad (2)$$

In our notation, the first (small case) subscript indicates the chemical species and the second (capital) subscript indicates the zone of interest. Subscripts a, te, le therefore denote analyte, TE and LE ions, respectively, while subscripts A, T, L denote analyte, TE and LE zones.

Whether and when the ITP focusing conditions given by Eqs. (1) and (2) are valid depends strongly on local conditions, as effective mobility is a strong function of pH and a weaker function of ionic strength. For example, the effective mobility of a weak acid analyte increases monotonically with increasing pH, and saturates at the lowest (negative) valence. Conversely, the effective mobility of a weak base decreases with increasing pH may saturate at the highest valence. In this work, we will consider only singly ionized ions so that the aforementioned saturation values are the fully-ionized mobilities of the +1 cation and –1 anion, respectively.

Figure 1B:
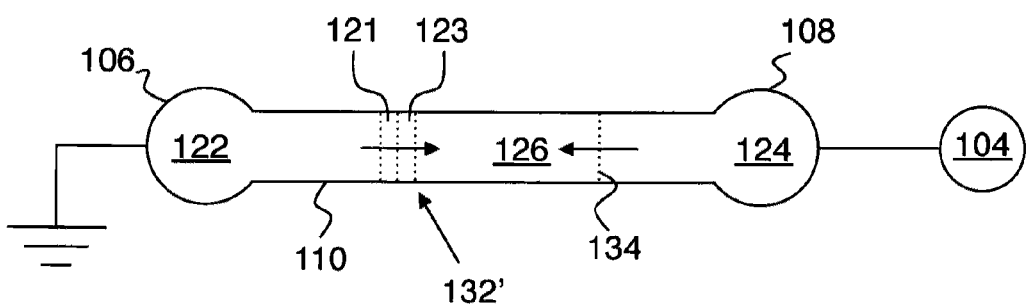
Figure 1C:
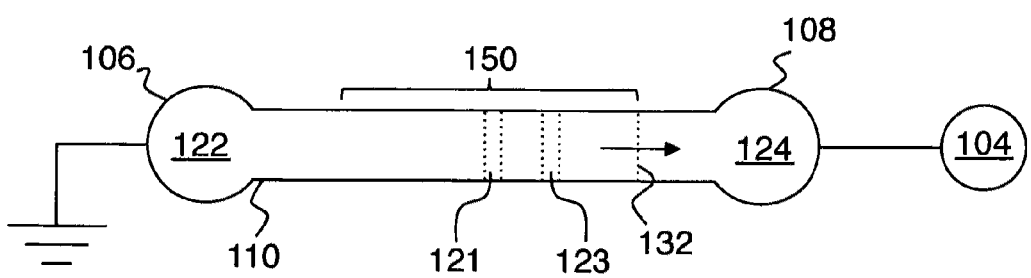

In this work we use bidirectional ITP with converging shocks to quickly and precisely alter the pH of migrating ITP zones so that analytes isotachophoretically focus before the shock interaction, and electrophoretically separate thereafter. FIGS. 1a-c show a schematic of our technique.

FIG. 1a shows an initial condition. Here a channel 110 is initially filled with a mixture 126 of LE+, LE– and analytes S1– and S2–. The left reservoir 106 is filled with a mixture 122 of LE+/TE–, while the right reservoir 108 is filled with a mixture 124 of TE+/LE–. Buffers are chosen such that LE+ is a cation of a weak base with high mobility and TE+ is a cation of a strong base with low mobility. Furthermore, LE– is an anion of a strong acid with high mobility and TE– is an anion of a weak acid with low mobility. For anionic ITP we choose LE–, TE– and background counter-ion (LE+) such that ITP focusing conditions (1) and (2) hold for analytes S1– and S2– prior to the shock interaction.

FIG. 1b shows analyte focusing after application of a voltage from a voltage source 104. When voltage is applied, the anionic analytes S1– and S2– focus between LE– and TE– at regions 121 and 123. The focused analyte zones 132' propagate towards the right, as shown. Simultaneously, a leftward-propagating cationic ITP shock 134 forms between LE+ and TE+ zones. Because TE+ is a stronger base than LE+, TE+ raises the pH behind the LE+/TE+ shock.

FIG. 1c shows analyte separation after shock wave interaction. The LE+/TE+ shock 134 sweeps over the focused anionic analyte zones 132', replacing the local LE+ counter-ions with TE+ ions. In this newly created interaction region 150, where TE+ ions replaced the LE+ ions, the pH and effective mobilities of the buffer and analyte ions change. To initiate electrophoretic separation in the interaction region, we choose the conditions such that the effective mobility of TE– in the newly created zone is larger than the effective mobilities of S1– and S2–. This causes TE– ions to overtake and pass the analyte zones. Thereafter, S1– and S2– separate, as in capillary zone electrophoresis. The resulting configuration, e.g., as shown on FIG. 1c, has separated analyte regions 121 and 123 within an interaction region 150 formed by the interaction of the ITP shock waves. In this example, interaction region 150 does not have a sharply defined left boundary. Instead, this boundary is a diffused boundary. The reason for this is that the LE+/TE+ shock wave 134 may or may not persist after the shock wave interaction. If it persists, shock wave 134 can be taken to be the left boundary of interaction region 150. If shock wave 134 does not persist (which is the case shown on FIG. 1c), the left boundary of interaction region 150 is a diffused boundary. Practice of the invention does not depend critically on the nature of the interaction region boundaries (i.e., sharp or diffused).

In this example, the cationic ITP interface plays no role in the initial ITP focusing of analytes at the anionic ITP interface. The purpose of cationic ITP is to initiate electrophoretic separation of these analytes upon interaction of the anionic and cationic ITP shocks. We note that our technique, therefore, differs markedly from unidirectional transient ITP (t-ITP), where LE ions are injected behind focused anionic samples to initiate separation.

There are several choices to be made in designing ITP shock interactions which initiate electrophoretic separation. We here focus our discussion on choosing electrolytes (LE+, LE–, TE+, and TE–) to preconcentrate and separate strongly ionized analytes, such as nucleic acids. However, we note that our technique is also applicable to a wide variety of cases including that of weak electrolyte species. For the case of strongly ionized analytes, we choose a high fully ionized mobility (absolute mobility) weak base for the LE+, and stronger base with low mobility for TE+. This creates a pH gradient across the initial LE+/TE+ shock, with a higher pH on the cationic TE+ side. For the anionic ITP component, we choose from relatively strong acids for LE–. We then choose a weaker acid for TE–, but one which has a high fully-ionized mobility. The latter is the key choice as we will use bidirectional ITP to effect a titration of the TE– (weak acid) to create TE– ions which overtake analyte ions after the shock interaction.

After the shock interaction, TE+ (cation of strong base) replaces LE+ (cation of weak base) as the counter-ion for anionic ITP. This increases the local pH of anionic ITP zones and therefore raises the raises the local value of effective mobility of TE– ions. In contrast, the effective mobilities of LE– ions and the anionic analytes do not change appreciably after the shock interaction as they are anions of relatively stronger acids. If we make these choices correctly, the shock interaction causes the effective mobility of TE− to increase to a value larger than that of analyte ions. This then violates the ITP focusing condition given by Eq. (1) and initiates electrophoretic separation.

This transition from focusing to separation is somewhat analogous in function to t-ITP. However, in t-ITP LE ions are injected behind the focused analytes (typically by deactivating applied current and effecting a buffer exchange at the TE reservoir) to initiate electrophoretic separation. Here we use the titration caused by the interaction between cationic and anionic ITP shocks to effect a change in the mobility of TE ions, such that they themselves overtake the focused analytes. Our method therefore features an initial condition which governs both focusing and separation dynamics, and the transition from ITP to separation can be initiated automatically with no buffer exchange or intermediate injections. As we show below, our method also achieves this transition with much less dispersion of the focused analytes compared to that in t-ITP.

We here provide specific examples of viable electrolyte chemistries for our method. Note that a key requirement is that the LE+ should be a cation of a weak base with high fully-ionized mobility, while TE+ should be a cation of a strong base with low fully-ionized mobility. For strong base, fast cations we can use $Na^+$ and $K^+$. However, several choices exist for high fully-ionized mobility cations of weak bases and low fully-ionized mobility cations of strong bases. Table 1 below shows three choices each for cationic LE and TE (nine usable combinations of LE+ and TE+) which satisfy our requirements. Another requirement is that the effective mobility of TE− ions should be less than that of analyte ions when the buffering counter-ion is LE+ and otherwise when the counter-ion is TE+. In order to effect a substantial increase in effective mobility of TE− after the shock interaction, TE− should therefore be a weak acid such that $pK_{a,LE-} < pK_{a,TE-} < pK_{a,TE+}$. For example, in our experiments we used Tricine ($pK_{a,TE-}$=8.15) as TE− along with Imidazole ($pK_{a,LE+}$=7.15) as LE+ and Arginine ($pK_{a,TE+}$=8.92) as TE+. On the other hand, there are no specific constraints on LE−, which can be any fast ion such as $Cl^-$ and $SO_4^{2-}$.

We note that our bidirectional ITP experiments are compatible with both "semi-infinite" and "finite" sample injection schemes. For example, in FIG. 1a we show a semi-infinite sample injection scheme, where sample ions are initially mixed in the LE−/LE+ mixture 126. Such an injection scheme both increases sensitivity (by continuously focusing sample until the shock interaction), and minimizes the complexity of the injection protocol. Alternatively, semi-infinite sample injection can be performed by mixing the sample ions in the TE−/LE+ reservoir. As a third alternative, sample ions can be injected using a more traditional finite injection protocol, wherein a finite amount of analyte mixture is initially sandwiched between pure LE−/LE+ and TE−/LE+ zones. However, we emphasize that the choice of sample injection scheme does not have a significant effect on the transition from ITP to CE mode or the quality of CE separation.

TABLE 1

Possible cationic buffer systems for coupled preconcentration and separation of anions using bidirectional ITP.

| | $\mu_{+1}$ (×10$^{-9}$ m$^2$V$^{-1}$s$^{-1}$) | $pK_{a,+1}$ |
|---|---|---|
| cationic LE (LE+) | | |
| Imidazole | 52 | 7.15 |
| 3-methyl pyridine | 40.1 | 5.5 |
| 2-methyl pyridine | 40.1 | 6.2 |

TABLE 1-continued

Possible cationic buffer systems for coupled preconcentration and separation of anions using bidirectional ITP.

| | $\mu_{+1}$ (×10$^{-9}$ m$^2$V$^{-1}$s$^{-1}$) | $pK_{a,+1}$ |
|---|---|---|
| cationic TE (TE+) | | |
| Arginine* | 26.9 | 8.92 |
| Tris | 29.5 | 8.08 |
| Amediol | 33.5 | 8.78 |

*Arginine has two other ionization states corresponding to $pK_{a,-1}$ = 12.48 and $pK_{a,+2}$ = 1.78. However, Arginine is primarily disassociated in its +1 state under safe pH conditions of 5 < pH < 9.

Figures 2A, 2B:
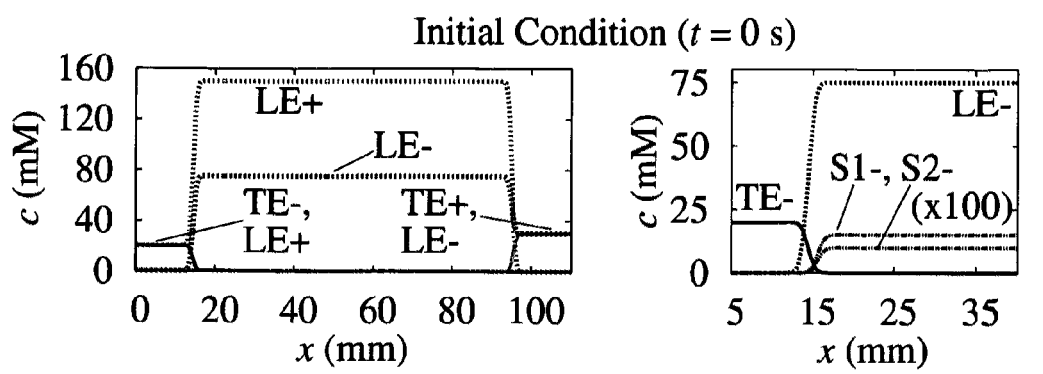
FIGS. 2a-h show simulation results relating to the focusing to separation mode.
Figures 2C, 2D:
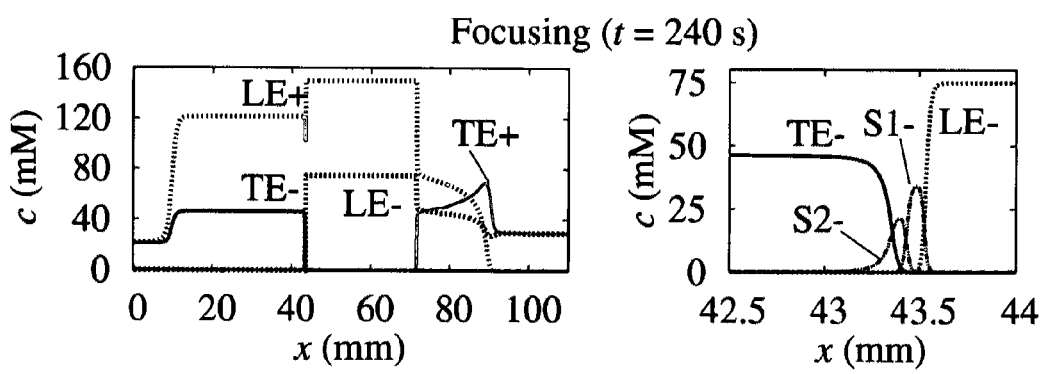
Figures 2E, 2F:
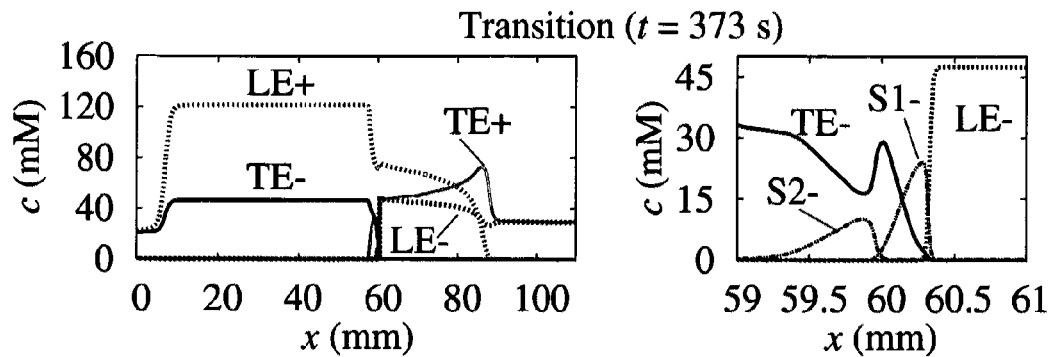
Figures 2G, 2H:
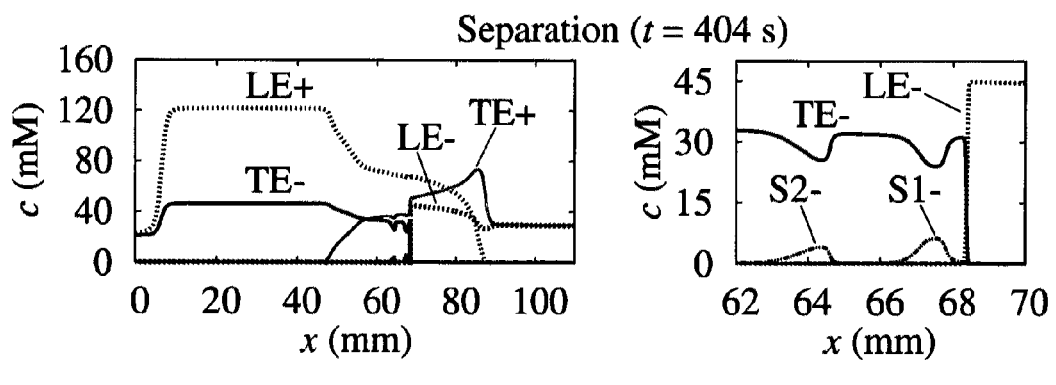

A2.2) Simulations of Bidirectional ITP for Both Focusing and Separation of Analytes We performed simulations of coupled ITP focusing and electrophoretic separation of two model analytes in bidirectional ITP using the SPRESSO simulation tool. For our simulations we used 75 mM HCl as LE−, 20 mM Tricine as TE−, 150 mM Imidazole as LE+ and 30 mM Arginine as TE+. To illustrate the technique we used two model anionic analytes S1− and S2− for the simulation with mobilities −20×10$^{-9}$ m$^2$Vs$^{-1}$ and −12×10$^{-9}$ m$^2$Vs$^{-1}$, respectively. These analytes were assumed to be fully ionized under the conditions of simulation. The results are shown on FIGS. 2a-h. Plots in the second column are detailed views of the distributions in the first column. FIGS. 2a-b show the initial distribution of chemical species in the separation channel, prior to activating current. FIGS. 2c-d show LE−/TE− and LE+/TE+ shocks after the electric field is applied. FIG. 2c shows an LE−/TE− shock (x=43 mm) propagating rightward and a LE+/TE+ shock (x=70 mm) propagating leftward. FIG. 2d shows anionic analytes S1− and S2− focused between LE− and TE−. FIGS. 2e-f show the transition from focusing to separation upon the interaction of LE−/TE− and LE+/TE+ ITP shocks. The high pH TE+ zone washes over the focused anionic analytes, increasing the effective mobility of TE− ions, while only negligibly affecting the mobility of S1− and S2− which are stronger acids. Here, the effective mobility of TE− increases above those of S1− and S2−, thereby initiating separation. FIG. 2f shows TE− overtaking focused S1− and S2−, thus initiating electrophoretic separation. FIG. 2g-h show the final state, in which analytes S1− and S2− are fully separated. FIG. 2g shows an anionic ITP shock at x=68 mm and an expansion wave (x=50 mm) due to disrupted cationic ITP. FIG. 2h shows fully separated peaks of S1− and S2−, but an intact ITP interface between LE− and TE−. We assumed a constant current of 1.4 µA, and a D-shaped, wet-etched channel 74 µm wide and 12 µm deep. We approximately account for electroosmotic flow using a constant and uniform electroosmotic mobility of 2×10$^{-9}$ m$^2$Vs$^{-1}$.

FIGS. 2a-b show the initial conditions of the simulation. Analytes S1− and S2− were initially mixed in the LE−/LE+ mixture at a concentration of 15 µM and 10 µM, respectively. When electric field is applied, LE−/TE− and LE+/TE+ shocks propagate towards the right and the left, respectively. Prior to shock interaction, analytes S1− and S2− focus between the LE− and TE− ions, as shown in FIG. 2d. For this particular buffer chemistry, LE+ and TE+ form a shared cationic ITP zone as shown in FIG. 2c. (We see a shared zone since the effective mobility of LE+ ions in the TE+ zone is smaller than that of TE+ ions, but the effective mobility of LE+ ions in the LE+ zone is greater than that of TE+ ions.) When the LE+/TE+ and LE−/TE− shocks interact (FIGS. 2e-f) the effective mobility of TE− increases and it overtakes the focused analytes S1− and S2−. This initiates electrophoretic separation of S1− and S2−. FIGS. 2g-h show the final state where both analyte ions, S1− and S2−, are fully separated. We note that, for electrophoretic separation to occur it is necessary for TE− ions to overtake the focused analytes. However, TE− ions need not overtake LE− ions and the LE−/TE− shock may persist, as shown in FIGS. 2g-h. In contrast, the shock interaction interrupts the LE+/TE+ interface and this interface mixes (via electromigration dispersion) thereafter. That is, after the shock interaction, TE− replaces LE− as the counter-ion for cationic ITP. Since the conjugate acid of TE− is weaker than the conjugate acid of LE−, the pH of cationic ITP zones increases after the shock interaction. As a result, the effective mobility of LE+ (cation of a weak base) decreases considerably compared to TE+ (cation of a strong base), causing disruption of the cationic ITP interface.

Simulation results, shown in FIGS. 2a-h highlight the advantages of focusing and separation using bidirectional ITP over t-ITP. As shown in FIGS. 2e-f, TE− ions begin overtaking focused analyte ions (S1− and S2−) as soon as the LE+/TE+ shock wave washes over the focused analyte ions. Thus, the transition from focusing to separation occurs quickly after shock interaction. This is in contrast with t-ITP, in which LE ions injected behind the TE zone must first overtake the entire TE zone before disrupting the ITP focusing. More importantly, in t-ITP, LE ions injected behind the TE zone first tail into analyte zones and effect a longer, more gradual disruption of ITP focusing. The latter can lead to significant electromigration dispersion of the analyte zones prior to separation. Here we observe a rapid change of local electromigration conditions (from ITP to zone electrophoresis separation) during which we observe negligible dispersion. (In Sec. A2.3 we compare the separation resolution of bidirectional ITP and t-ITP using numerical simulations.) Rapid transition from ITP to CE in our technique is especially important for on-chip systems where channel lengths may be limited. Finally, the transition from focusing to separation in bidirectional ITP is fully automated and does not require buffer replacement or switching electric field between column-coupled channels as in t-ITP. Thus the current technique can be easily adapted for on- or off-chip single channel systems, including commercial CE systems.

We also performed a simulation at conditions where we can directly compare numerical predictions with experimental visualization of interacting shocks waves. For this, we used the same ITP chemistry and the initial conditions as in the previous simulation (FIGS. 2a-h), but instead of analytes S1− and S2−, we used a fluorescent non-focusing tracer (NFT). The NFT does not disturb or change the ITP or focus during ITP, but its concentration adapts to the local electric fields in each ITP zone (see FIG. 3a). Thus the regions of varying fluorescence intensity highlight and denote different ITP zones (more on NFT visualization technique in Sec. A4.1 below).

Figure 3A:
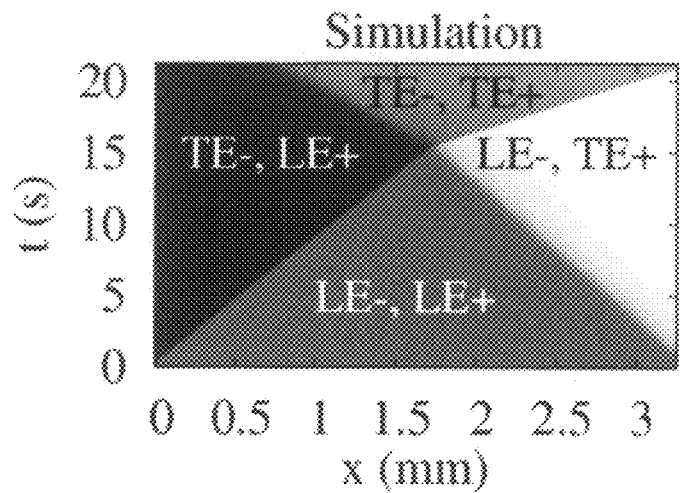
FIGS. 3a-b show a comparison between simulated and experimental results for the focusing to separation mode.
Figure 3B:
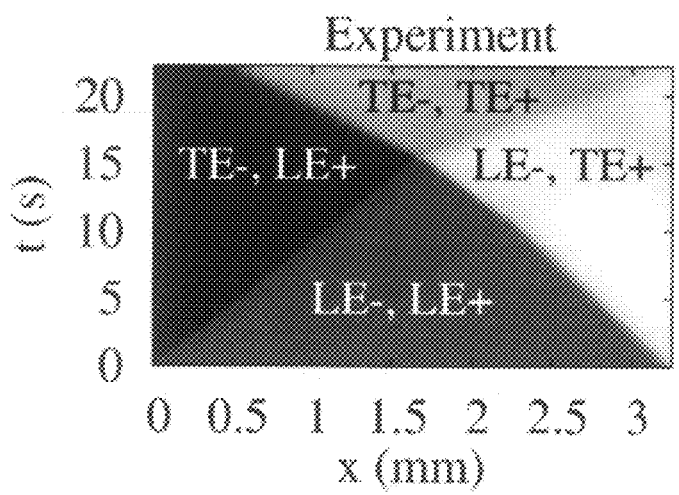

FIGS. 3a-b show numerical simulation and experimental visualization of interacting anionic and cationic ITP shocks. FIG. 3a shows numerical simulation of propagating LE−/TE− and LE+/TE+ shocks. The spatiotemporal plot shows the intensity of a fluorescent non-focusing tracer (NFT) versus distance along the channel axis, x, and time, t. The NFT does not focus via ITP, but its concentration adapts to the local electric field in each zone. Regions of different fluorescence intensity mark ITP zones. The scalar quantity plotted here is the fluorescence intensity of NFT (averaged along the channel width) as a function of distance along the axis of the channel (abscissa) and time (ordinate). Our simulation neglects the effects of photobleaching and we assume a linear relationship between fluorescence intensity and the NFT concentration. FIG. 3b shows experimental visualization of the same process using the fluorescent non-focusing tracer (NFT) technique. FIGS. 3a and 3b both show LE−/TE− and LE+/TE+ shocks propagating towards the right and left, respectively. These shocks meet near x=1.6 mm. The rightward traveling LE−/TE− shock remains intact (positive slope to the right of x=1.6 mm). In contrast, the LE+/TE+ interface is disrupted and the interface starts to mix (barely noticeable in this field of view). Here the zones gradually mix via electromigration dispersion. To account for electroosmotic flow in our simulation, we used a constant electroosmotic mobility of $2 \times 10^{-9}$ $m^2Vs^{-1}$ as our only fitting parameter to match all experimentally measured wave speeds (see Sec A4.1). We used Rhodamine 6G as the NFT. We applied 1.4 μA current across a D-shaped, wet-etched 74 μm wide and 12 μm deep channel.

A2.3) Comparison of Bidirectional ITP and Transient-ITP

Figure 4A:
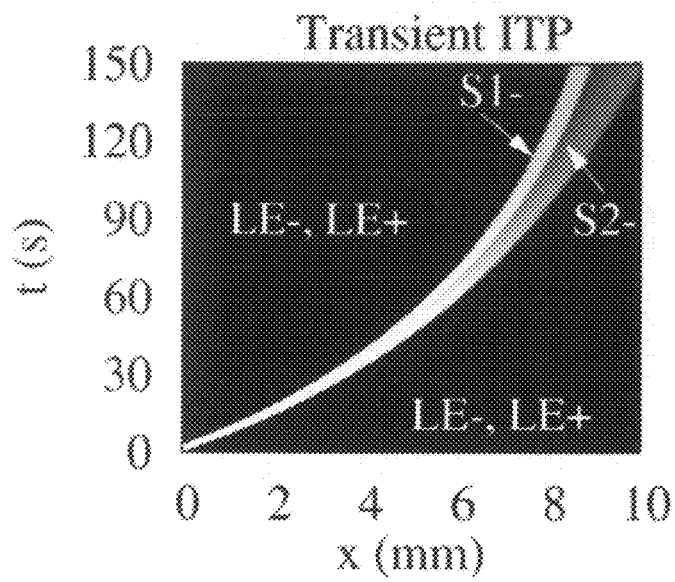
FIGS. 4a-b show a comparison between bi-directional ITP (focusing to separation mode) and transient ITP.
Figure 4B:
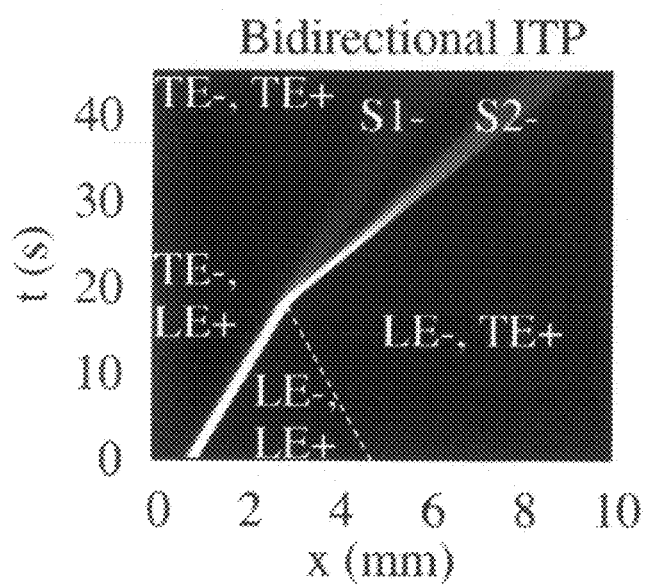

We here compare traditional unidirectional t-ITP and bidirectional ITP using numerical simulations. FIGS. 4a-b respectively show simulated spatiotemporal plots of these two cases. In both cases, we consider the same anionic analytes (S1− and S2−) as in FIGS. 2a-h but, to aid in visualization of various ITP zones, we also consider addition of a NFT which is initially mixed with the LE−/LE+ buffer. The background fluorescence intensity values in FIGS. 4a-b therefore correspond to the concentration of NFT in the various ITP zones, while the brighter zones correspond to the analyte peaks.

For the anionic t-ITP simulations, we used the anionic ITP chemistry (with LE+ as the counter-ion), channel geometry and applied current of the simulation of FIGS. 2a-h. Traditional anionic t-ITP does not involve cationic ITP, so we did not use TE+ in the t-ITP simulations. We first performed simulation of ITP focusing of analyte ions, S1− and S2−, between zones of LE− and TE− ions. We then stopped the simulation and replaced TE− ions in the TE−/LE+ reservoir (near the leftmost boundary) with LE− ions; this initiated the process of disrupting ITP. FIG. 4a shows S1− and S2− ions initially focused in a narrow ITP zone which propagates rightwards at a constant speed (the constant slope line for t<25). Around t=25 s and x=4 mm, LE− ions begin overtaking the focused analytes and initiate electrophoretic separation of S1− and S2−. FIG. 4a shows the separation phase of t-ITP for t>25 s, during which the distance between the analyte peaks increases over time, while the peaks themselves broaden due to diffusion and electromigration dispersion. Interestingly, during the transition from ITP focusing to CE separation, the speed of analyte zones decreases considerably. This deceleration of analyte zones is apparent in FIG. 4a, where the analyte peak locations vary nonlinearly with time after t=25 s. The transition phase in t-ITP is slow, analyte zones disperse, and the distance between the analyte peaks does not exceed their characteristic widths until about t=90 s.

For the bidirectional ITP simulation (FIG. 4b) we used the same conditions as those of FIGS. 2a-h, including the electrolyte chemistry, applied current and the channel geometry; the only difference being the presence of NFT in FIG. 4b. We note that the results shown in FIGS. 2a-h and 4b are quite similar, as the presence of the NFT in trace amounts (100 μM initial concentration) has a negligible effect on local electric fields, and focusing and separation of S1− and S2−. FIG. 4b shows the LE−/TE− shock wave propagating towards the right and the LE+/TE+ shock wave (white dashed line added to emphasize this feature) propagating towards the left (for t<25 s). Analytes S1− and S2− initially focus at the LE−/TE− interface. When the LE−/TE− and LE+/TE+ shock waves interact around x=4 mm and t=25 s, ITP focusing of S1− and S2− very quickly transitions to CE separation. Thereafter (for t>25 s), the relative distance between S1− and S2− peaks keeps increasing, while the peaks gradually diffuse over time.

Comparison of FIGS. 4a and 4b shows that the analyte peaks in bidirectional ITP are much better resolved than in t-ITP. That is, for the same distance between the two peaks, the peaks in bidirectional ITP are much less dispersed than in t-ITP. Bidirectional ITP yields higher resolution separations since the ITP-to-CE transition in bidirectional ITP occurs quickly after the anionic and cationic ITP shocks interact. Thus analytes are exposed to local conductivity gradients (which cause electromigration dispersion) for much shorter distance and time. In contrast, in t-ITP, LE− ions injected behind the TE− zone tail significantly into the focused analyte zones and only gradually and slowly disrupt ITP preconcentration, yielding significant and prolonged electromigration dispersion. In addition to better resolution, the faster ITP-to-CE transition offered by bidirectional ITP results in reduced separation time and increased signal-to-noise ratio for a given resolution. Compare for example the resolution obtained by bidirectional ITP in FIG. 4b at t=45 s. Such resolution is not observed in the t-ITP case (FIG. 4a) even at t=150 s.

A3) Materials and Methods

We performed experiments to visualize interacting cationic and anionic ITP shock waves in bidirectional ITP using the fluorescent non-focusing tracer (NFT) technique (c.f. Sec. A4.1). For these visualization experiments, LE− was the chloride ion from 75 mM HCl, TE− was 20 mM Tricine, LE+ was 150 mM Imidazole and TE+ was 30 mM Arginine. We prepared 10 mM stock solution of the Rhodamine-6G dye (Invitrogen, Carlsbad, Calif.) and used it as an NFT by mixing at a concentration of 100 µM in the LE+/LE− mixture.

For the experiments demonstrating coupled ITP preconcentration and separation of DNA fragments (Sec. A4.2) we used chloride ion from 150 mM HCl as LE−, 20 mM Tricine as TE−, 300 mM Imidazole as LE+ and 30 mM Arginine as TE+. We added a 1 kbp DNA ladder from New England BioLabs (Ipswich, Mass.) to the mixture of LE+ and LE−, with final concentration of 50 ng/ml. We used 0.75% w/w hydroxyl ethyl cellulose (HEC) as a sieving matrix (mixed with LE−) to achieve a size-dependence on the mobility of fragments, as the free solution mobility of ds-DNA fragments greater than ~400 bp is effectively independent of molecular weight. To visualize the DNA fragments, we used the fluorescent intercalating dye SYBR Green I (Invitrogen, Carlsbad, Calif.). (We note that intercalating dyes, such as SYBR Green I, should be handled carefully due to their potential mutagenic properties.)

We prepared 1 M stock solutions of HCl, Tricine and Imidazole, and 300 mM stock solution of arginine hydrochloride before diluting them to desirable concentrations in different solutions. We added 1% w/w polyvinylpyrrolidone (PVP) to all solutions in order to suppress electroosmotic flow. All chemicals were obtained from Sigma Aldrich (St. Louis, Mo.) and were prepared in UltraPure DNase/RNase free distilled water (GIBCO Invitrogen, Carlsbad, Calif.).

We captured images using an inverted epifluorescent microscope (IX70, Olympus, Hauppauge, N.Y.) equipped with a LED lamp (LEDC1, Thor Labs, Newton, N.J.), U-MWIBA filter-cube from Olympus (460-490 nm excitation, 515 nm emission, and 505 nm cut off dichroic) and a 10× (NA=0.3) UPlanApo objective (Olympus, Hauppauge, N.Y.). Images were captured using a 12 bit, 1300×1030 pixel array CCD camera (Micromax1300, Princeton Instruments, Trenton N.J.). We controlled the camera using Winview32 (Princeton Instruments, Trenton N.J.) and processed the images with MATLAB (R2007b, Mathworks, Natwick, Mass.). We conducted the experiments by applying either constant voltage or current using a sourcemeter (model 2410, Keithley Instruments, Cleveland, Ohio).

Figure 5A:
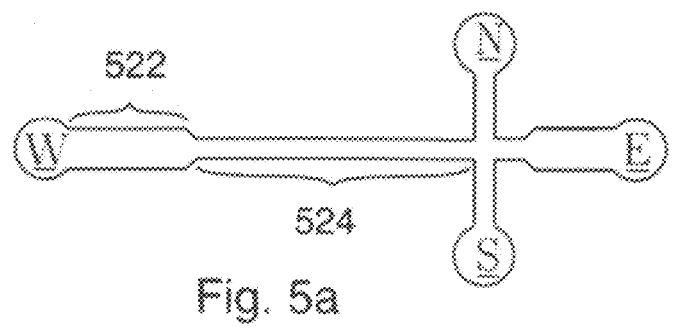
FIGS. 5a-e show an exemplary experimental protocol for DNA separation using bi-directional ITP in the focusing to separation mode.
Figure 5B:
Figure 5C:
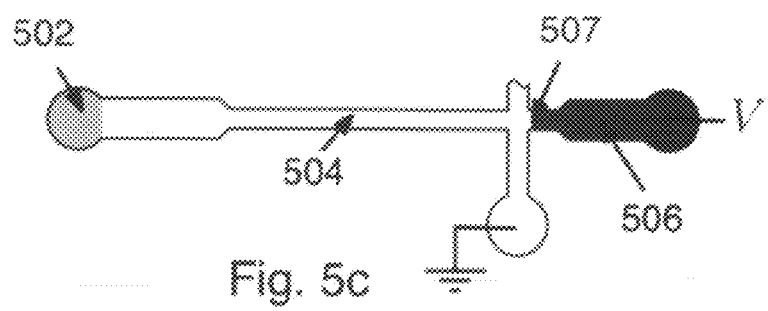

For all our experiments, we used off-the-shelf Caliper NS-95 borosilicate glass micro-chips from Caliper Life Sciences (Mountain View, Calif.). FIG. 5a shows a schematic of the channels with cross-geometry. The channels include a relatively wide loading section 522 (50 µm mask width) and a relatively narrow separation section 524 (10 µm mask width). All channels are wet etched to a depth of 12 µm. The variable cross-section geometry allows us to achieve higher sensitivity in ITP by focusing a large amount of sample in the loading section prior to entering the separation channel.

A4) Experiments

We first performed on-chip bidirectional ITP experiments to visualize interacting cationic and anionic ITP shock waves. For these experiments, we did not focus analytes, but instead visualized the interaction of cationic and anionic LE/TE interfaces. We used these visualization experiments to optimize our injection protocol to precisely control the location of shock interaction. We then performed bidirectional ITP experiments to demonstrate coupled preconcentration and high resolution separation of DNA fragments from 1 kbp ds-DNA ladder.

A4.1) Visualization of Interacting Shocks in Bidirectional ITP

We visualized interacting anionic and cationic ITP shocks in bidirectional ITP using the NFT technique. In the NFT technique, fluorescent, co-ionic species which do not obey the ITP focusing conditions given by Eqs. (1) and (2) are mixed with the ITP buffers. These fluorescent species do not focus, but their concentration adapts to local electric field in different ITP zones in order to maintain the continuity of electromigration flux. For our experiments, we used 100 µM concentration of Rhodamine-6G (R6G, a cationic dye) in the LE+/LE− mixture as the NFT. In our experiments R6G is slower than the cationic TE ions and so does not focus. Hence, we visualized propagating anionic and cationic ITP shock waves simultaneously using a single non-focusing fluorescent species (Rhodamine-6G).

FIG. 3b shows an experimentally measured spatiotemporal plot of fluorescence intensity in a bidirectional ITP experiment with converging shock waves. To obtain this spatiotemporal plot, we captured CCD camera images of fluorescence intensity in a 3.25 mm long section of the channel at a rate of 10 frames per second. We then width-averaged the fluorescent intensity for 210 images and plotted this axial intensity distribution for each point (in time) along the ordinate. In FIG. 3b, the abscissa is axial distance along the channel, the ordinate is time, and the intensity of plotted scalar is the measured fluorescence intensity. The slopes of features in such spatiotemporal plots are therefore inversely proportional to the velocities of ITP zone interfaces. FIG. 3b shows that, prior to the shock interaction (t<15 s), the LE−/TE− shock propagates towards the right and the LE+/TE+ shock towards the left. After the LE−/TE− and LE+/TE+ shocks interact (at x=1.6 mm and t=15 s), the LE+/TE+ interface is disrupted and a rarefaction wave ensues. This is because the effective mobility of TE+ becomes higher than LE+ after the shock interaction. However after the shock interaction (t>15 s), the LE−/TE− interface remains intact as the mobility of fully-ionized chloride ion (LE−) remains higher than the effective mobility of Tricine (TE−) throughout the experiment. Our experimental visualization results compare well with the simulated spatiotemporal diagram shown in FIG. 3a. Our simulations correctly predict the persistence of LE−/TE− interface and the disruption of LE+/TE+ interface after the shock interaction. We use an electroosmotic mobility value of $2\times10^{-9}$ m²Vs⁻¹ as the only fitting parameter, and yet the simulations correctly predict the time and the location of shock interaction and the four observable propagation velocities.

We note that experimental visualization and simulations of interacting shocks in bidirectional ITP are particularly helpful in tuning the initial conditions to precisely select the location of shock interaction and transition from ITP focusing to electrophoretic separation. For our experiments on DNA separations (Sec. A4.2) we used a NFT to tune our injection protocol to initiate electrophoretic separation as soon as the focused analytes entered the narrow separation channel. This allowed us to obtain higher resolution by using the entirety of the separation channel for the CE mode.

A4.2) Coupled Preconcentration and Separation of DNA Fragments

We performed experiments to demonstrate coupled ITP preconcentration and electrophoretic separation of DNA fragments using bidirectional ITP. The injection protocol for these experiments is shown in FIGS. 5*a-e*. For separation experiments with finite sample loading: (FIG. 5*a*) we injected the mixture 504 of LE+, LE− and DNA fragments by applying vacuum on W well. We then emptied E and W wells and (FIG. 5*b*) filled E and W wells with TE+/LE− mixture 506 and LE+/TE− mixture 502, respectively. (FIG. 5*c*) We then moved the LE+/TE+ interface 507 up to the E-W to N-S junction by applying voltage between E and S wells. We performed this optional step to ensure that the LE−/TE− and LE+/TE+ shocks interacted precisely near the entrance of the separation channel 524 (the smaller cross-section channel). (FIG. 5*d*) We then switched the electrodes so that voltage is applied between the E and W wells. (We note that precaution should be taken and the high voltage supply should be turned off while manually switching electrodes as shown in FIGS. 5*a-e*.) The LE+/TE+ shock meets the focused DNA fragments 508 and initiates electrophoretic separation. (FIG. 5*e*) We imaged the separated DNA fragments 514 at the end of the separation channel using a detector 516. The injection protocol for semi-infinite injection of samples is similar, except that the analytes of interest (here DNA fragments) are initially mixed with LE+/TE− mixture in the W well. No manual buffer exchanges are needed once voltage is applied, and we stress that the voltage switching used here is optional.

Figure 5D:
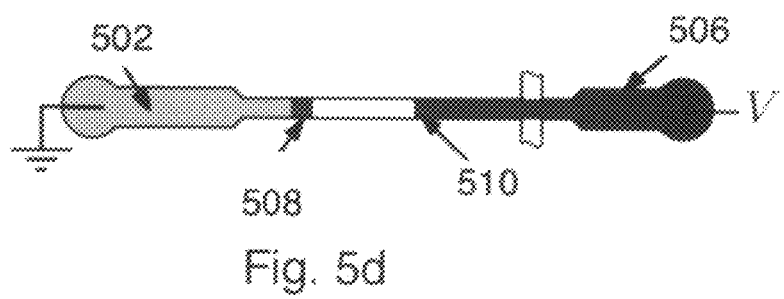
Figure 5E:
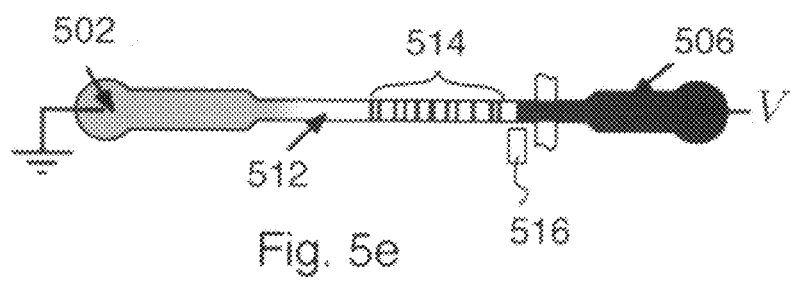

As shown in FIG. 5*d*, prior to the shock interaction, the 1 kbp ds-DNA ladder is focused between the LE− and the TE− zones (i.e., at 508). When the LE+/TE+ shock washes over the focused DNA fragments, both the pH of the TE− zone and the effective mobility of TE− ions increase. However, under the conditions of our experiments (pH>7), DNA fragments are fully ionized and any increase in pH has no significant effect on the effective mobility of DNA fragments. TE− ions, therefore, overtake focused DNA after the shock interaction, initiating electrophoretic separation in the HEC sieving matrix (shown schematically in FIG. 5*e*). In our experiments, we used a semi-infinite injection scheme by mixing DNA fragments with the LE− and LE+ mixture in order to increase the sensitivity by continuously focusing DNA fragments until the shock interaction. We note that the DNA fragments can also be initially mixed with LE+/TE− mixture.

FIGS. 6*a-d* show the results. FIG. 6*a* (inset) shows initially focused DNA fragments in anionic ITP. FIG. 6*b* (inset) shows the transition from focusing to CE separation after the cationic ITP interface washes over the focused DNA fragments. FIG. 6*c* shows an electropherogram measured at the end of separation channel showing a fully resolved DNA ladder consisting of distinct peaks 1 to 11 corresponding to the 10, 8, 6, 5, 4, 3, 2, 1.5, 1, 0.517, and 0.500 kbp fragments. The electropherogram of FIG. 6*c* is measured 15 mm to the right of the point where the shocks interact. For this experiment we used a semi-infinite injection of DNA sample to increase the detection sensitivity and minimize the injection complexity. FIG. 6*d* shows visualization (inverted) of agarose gel electrophoresis separation (provided by the vendor, New England BioLabs, Ipswich, Mass.). We note that peaks 10*a* and 10*b* (corresponding to 500 and 517 bp) are clearly resolved by our technique (see FIG. 6*c*) but not resolved in agarose-gel electrophoresis (e.g., FIG. 6*d*). For these experiments, we diluted the DNA to 50 ng/ml concentration in the LE+/LE− mixture with only 1 pg DNA initially injected into the separation channel.

A5) Conclusions

We have developed a new technique to automatically couple isotachophoretic preconcentration and electrophoretic separation via shock interaction in bidirectional ITP. We have described how interaction of cationic and anionic ITP shocks in converging bidirectional ITP can lead to fundamental changes in focusing behavior of analytes. We leveraged shock interaction in bidirectional ITP to precisely change the pH of migrating zones, so that initially focused analytes initiate electrophoretic separation upon shock interaction. To the best of our knowledge, this is the first time that shock interaction in bidirectional ITP has been leveraged to couple different electrophoresis modes.

We discussed practical choices of electrolyte chemistries for bidirectional ITP which give electrophoretic separation after the interaction of cationic and anionic ITP shocks. To illustrate the technique and verify our choice of buffer chemistry we performed numerical simulations using 1-D area averaged electromigration-diffusion transport equations. Based on these simulations, we showed that the transition from focusing to separation in bidirectional ITP is fast and results in negligible electromigration dispersion of electrophoretic zones. We confirmed the simulation results with indirect fluorescence visualization experiments of bidirectional ITP zones. Using a single fitting parameter (electroosmotic mobility) we showed that our simulations capture accurately the observed dynamics of shock interaction, including shock velocities and disruption of ITP interfaces after shock interaction. We then used simulations to compare separation resolution of bidirectional ITP and unidirectional t-ITP. Our simulations show that bidirectional ITP yields separations with significantly higher resolution and shorter analysis time compared to t-ITP. Finally, as an example application we used bidirectional ITP to couple ITP preconcentration and high resolution electrophoretic separation of DNA fragments of a 1 kbp DNA ladder. We fully resolve the ladder in 7 min (only 3 min after shock interaction) starting from a 30 μl sample dispensed into chip reservoir at 50 ng/ml concentration (after which ~1 pg of DNA injected into the channel) and using no manual steps.

Shock interaction in bidirectional ITP is an elegant way to couple ITP preconcentration and electrophoretic separation. The method eliminates the need for intermediate steps such as buffer exchange and deactivation and re-activation of a power supply. Unlike t-ITP, transition from focusing to separation in bidirectional ITP occurs over a relatively small distance (here order 1 mm) allowing optimal use of channel length for the ITP focusing and electrophoretic separation phases. This aspect is particularly important for on-chip systems which have constraints on maximum channel length. The technique can also be applied to conventional single channel CE systems (e.g., using fused silica capillaries), and eliminates the need of column-coupled channels for buffer replacement.

B) Focusing to Focusing Mode

B1) Introduction

In ITP, analytes present in sufficient amounts will focus and segregate into distinct "top hat" zones with uniform concentrations. This ITP mode is called "plateau mode" ITP because it is characterized by relatively long zones of locally uniform concentrations separated by thinner zone boundaries. For trace quantities, analyte species may not develop into such plateaus. Instead, multiple trace analyte species bounded by TE and LE focus into nearly completely overlapping peaks whose widths are governed by the diffuse TE-to-LE interface. This regime is termed "peak mode" ITP. Unlike plateau mode ITP, two adjacent zones in peak mode are practically indistinguishable from each other. Of course, a system with multiple analytes with a wide range of concentrations can form a "mixed mode" ITP condition. In mixed mode, depending upon their amounts, some analytes form peaks while others form plateaus.

Plateau mode ITP allows separation and detection of multiple analytes. Methods of analyte detection include a wide range of physico-chemical properties, such as local conductivity, UV absorbance, or temperature. Alternatively, the displacement physics of plateau mode ITP can be leveraged to detect analyte zones using indirect detection techniques, as in the fluorescent non-focusing tracer technique. Typical isotachopherograms obtained from all of these measurement methods have steps in the measured quantity (e.g., conductivity or fluorescence) corresponding to different ITP zones. The width of these steps is proportional to the amount of focused analytes, and the ability to detect trace amount of analytes is limited by the width of the zones relative to the thickness of diffused boundaries. Therefore, signal-to-noise ratio (SNR) in plateau mode ITP can be defined as the length of analyte zone normalized by the characteristic length of diffusive zone boundaries.

The sensitivity of plateau mode ITP detection is improved by increasing plateau zone width relative to the diffusive length of interfaces. Interface widths often scale inversely with electric field and can be affected by advective dispersion and the mobility difference between analytes and background ions. Several methods exist which can be used to increase the zone lengths in plateau mode ITP. These include: (i) longer separation channels, (ii) the application of hydrodynamic counter-flow, (iii) using channels with converging cross-sections, and (iv) using concentration cascade of the LE in the so-called "cascade ITP" technique. All these techniques favor a longer sample accumulation time prior to the detection, and thereby increase plateau zone lengths. Longer analysis time also increases the separation capacity of the system as analytes in the initial mixture have longer time to separate into purified zones. All or some of these techniques can be coupled to increase detection sensitivity, largely without affecting their individual performance. Therefore, these techniques can be studied and optimized independently before their integration.

In ITP, the concentration of plateau zones scales proportionally to the concentration of the LE zone. Analytes can be said to "adjust" to a concentration "set" by that of the LE and an order unity (typically <1.0) multiplier associated with the system's ion mobilities. Cascade ITP leverages this feature by focusing analytes sequentially using two LE zones. Analytes are first focused using a high concentration LE which increases sample loading and separation capacity; subsequently, analytes are detected using a low concentration LE. Analyte zones migrate from regions formerly occupied by the first LE into regions formerly occupied by the second LE and, as they do so, their concentration adjusts to a lower value set by the low concentration LE. Conventional cascade ITP typically requires a pre-set, physical separation between zones of high and low concentration LE. This separation has been accomplished using a column coupling arrangement (basically a T-junction) and/or through the use of valves. These requirements complicate the application of cascade ITP and have excluded the integration of cascade ITP into a simple, single channel architecture. These requirements also require an actuation step (of electrodes and/or valves) mid-way into the assay.

We here present a novel method of creating a concentration cascade of LE. Our method requires no actuation and can be achieved in a single, straight channel system. We effectively "chemically" transition from one LE to another by using bidirectional isotachophoresis. Bidirectional isotachophoresis involves simultaneous anionic and cationic ITP in a single channel, and is characterized by anionic and cationic ITP shocks propagating either towards or away from each other. In the current work, we use a bidirectional ITP mode where the anionic and cationic shock waves approach each other and interact to modify the electrophoresis conditions. Prior to shock wave interaction, analytes are subject to a relatively high concentration LE. Shock wave interaction then causes a sudden decrease of the LE ion concentration in the region ahead of the analytes. The technique can be used with either anionic or cationic ITP, removes the requirement of physical separation, and can be "programmed" into an ITP process in a single, straight channel by the initial electrolyte chemistry in the channel and the end-channel reservoirs.

We begin by describing our method of creating a concentration cascade of LE using bidirectional ITP. We then present an analytical model to predict the increase in zone length due to shock interaction and to provide predictions for the increase in detection sensitivity. We also present detailed numerical simulations to illustrate our technique. We confirm these simulations using experimental visualization of cascade ITP process in bidirectional ITP. We then present a series of controlled bidirectional ITP experiments with various electrolytes which show maximized detection sensitivity. Lastly, we employ our technique for the high-sensitivity, indirect-fluorescence-based detection of 2,4,6-trichlorophenol (a carcinogenic pollutant).

B2) Materials and Methods

B2.1) Concept of Creating Concentration Cascade of LE Using Bidirectional ITP

Bidirectional ITP involves simultaneous anionic and cationic ITP and is characterized by anionic and cationic ITP shock waves which propagate towards each other. Bidirectional ITP experiments require two oppositely charged pairs of LE and TE, which we here term as LE+, TE+, LE−, and TE−. LE and TE again denote the leading and trailing electrolyte ions, respectively, and + and − correspond to cations and anions respectively. Depending on the initial conditions, shocks in bidirectional ITP can be made to propagate either towards or away from each other. In the former mode, anionic and cationic ITP shocks eventually interact and result in the formation of new ITP zones. Electrophoretic conditions in these newly created zones can differ markedly from those prior to the shock interaction. For example, shock interaction can change the identity of the counterion species, the concentration of co-ion species, local ionic strength, and pH; and this can set new focusing or separation conditions for analytes.

In this section, we use shock interaction in bidirectional ITP to initiate a decrease in concentration of LE− ions and thereby elongate the zones of focused anionic analytes (consistent with cascade ITP). That is, prior to the shock interaction we focus anions with a high concentration LE− and then have shock interaction suddenly decrease the concentration of LE− ahead of the focused anions. Under these modified ITP conditions, the focused analyte zones are forced to readjust to lower concentrations. This decrease in the concentration of analyte zones, after the shock interaction, is accompanied by a corresponding increase in the zone lengths. Although we here explore anionic ITP in general, our technique is equally applicable to increasing the sensitivity of cationic ITP by creating a gradient in LE+ concentration.

Figure 7A:
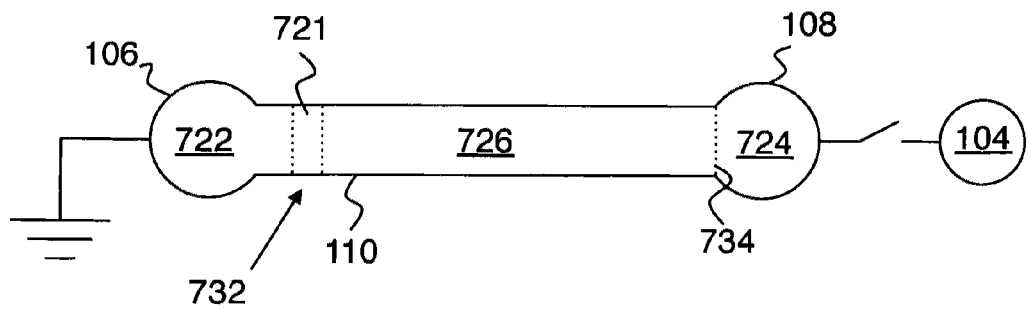
FIGS. 7a-c show operation of a ITP focusing to focusing mode of embodiments of the invention.
Figure 7B:
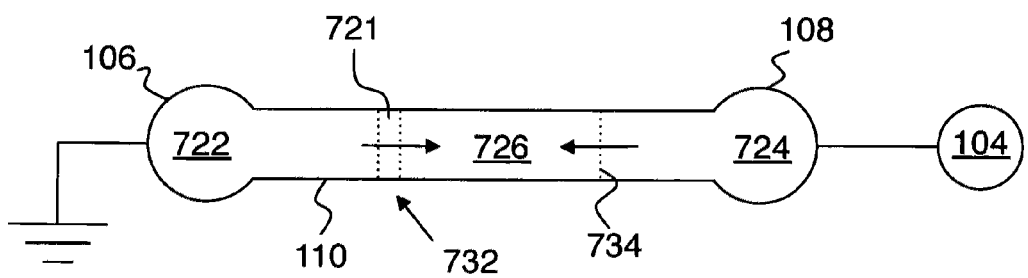
Figure 7C:
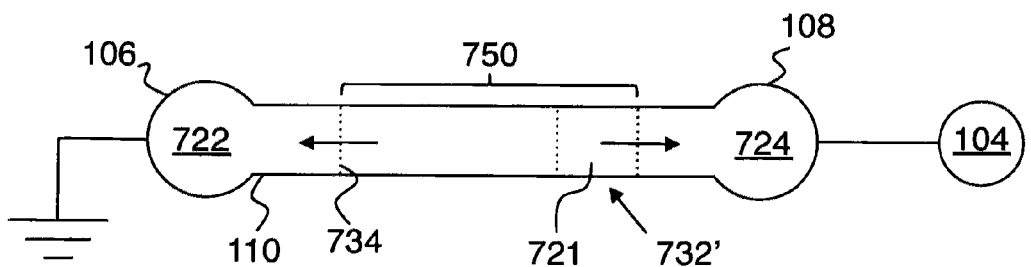

FIGS. 7a-c show an example of this approach. (FIG. 7a) The channel 110 is initially filled with a mixture 726 of LE+ and LE−. The left reservoir 106 is filled with a LE+/TE− mixture 722, while the right reservoir 108 is filled with a TE+/LE− mixture 724. The sample ions S− (721) are initially injected between the LE− and TE− zones. Buffers are chosen such that LE+ and TE+ are cations of weak bases and have respectively high and low mobility. LE− and TE− are anions with mobility higher and lower than that of S−, respectively. (FIG. 7b) When voltage is applied (e.g., from voltage source 104), the anionic analyte (S−) focuses between LE− and TE− and the analyte zone 732 propagates towards the right. Simultaneously, a leftward-propagating cationic ITP shock 734 forms between LE+ and TE+. Because the local electric field in the LE−/TE+ zone 724 is higher than that in the LE−/LE+ zone 726, the counterions (LE−) electromigrate faster behind the LE+/TE+ interface. Therefore, in order to balance the electromigration flux of LE− across the LE+/TE+ interface 734, the concentration of LE− drops in the LE−/TE+ zone 726. (FIG. 7c) When the LE+/TE+ shock 734 interacts with focused S− analyte zone 732, the latter finds a lower concentration LE− ahead of it. Consequently, the S− analyte zone 732' adjusts to a lower concentration and its zone length increases so as to conserve the mass of focused analyte.

To create a concentration cascade in LE−, we choose our electrolytes such that the concentration of LE−, the counterion for cationic ITP, drops significantly behind the cationic ITP shock (in the LE−/TE+ zone 724). Subsequently, when the cationic ITP shock meets the focused anionic analyte zone 732, LE−/TE+ zone 724 replaces the LE−/LE+ zone 726 as the leading electrolyte for anionic ITP. The low concentration of LE− in the LE−/TE+ zone 724 compared to the LE−/LE+ zone 726 causes the analyte zone to readjust to lower concentration. Consequently, the analyte zone length increases significantly (FIG. 7c). Later in Section B3.2 we discuss and quantify the choices of electrolyte chemistries which control and help maximize the zone length after the shock interaction.

In our technique, the cationic ITP does not affect the initial focusing of analyte ions in anionic ITP. The purpose of cationic ITP is: (i) to generate a gradient in LE− concentration, and (ii) to automatically trigger a change from high to low LE− concentration via shock interaction. In this way, our technique differs significantly from traditional cascade ITP wherein two unidirectional anionic ITP processes with different LE− concentration are coupled physically via valves or a column coupling arrangement.

We also note our scheme is compatible with both "finite" and "semi-infinite" injection schemes. In FIGS. 7b and 7c, we show a finite sample injection scheme where sample ions are initially sandwiched between LE−/LE+ and TE−/LE+ zones. Alternatively, to increase sensitivity and minimize complexity, sample ions can be mixed with the TE−/LE+ mixture 722 and allowed to focus continuously over time. In both cases, ITP focusing with high LE− concentration allows for greater sample loading prior to detection in the region formerly occupied by the low LE− concentration. We emphasize that an increase in lengths of anionic ITP zones occurs primarily due to the decrease in LE− concentration across the cationic ITP shock. Therefore, the injection method has no effect on the increase in zone length due to shock interaction. To illustrate these injection methods, we will here use both finite and semi-infinite injection schemes for our experiments (see Sections B3.4-B3.6).

B2.2) Materials and Instrumentation

We performed experiments to visualize and quantify the increase in analyte zone length due concentration cascade of LE in bidirectional ITP. We used the NFT technique for simultaneous visualization of all bidirectional ITP zones. For these visualization experiments, LE− was 100 mM Mops, TE− was 20 mM Taurine, LE+ was 280 mM Imidazole, and TE+ was 100 mM Bistris. We used a similar protocol as shown schematically in FIGS. 7a-c. To inject finite amounts of analytes, we first added Hepes and Tricine to the TE−/LE+ mixture at a concentration of 0.5 mM and 1 mM, respectively. We then allowed these analytes to focus until the analyte zones moved 5 mm from the TE− well. Subsequently, we replaced the mixture of analytes and TE−/LE+ with pure TE−/LE+, to effect a finite injection. We used a similar electrolyte chemistry and injection protocol for experiments demonstrating the effect of electrolyte composition on analyte zone length (Section B3.5). There, we varied the composition of LE−/LE+ mixture by fixing the concentration of LE− at 100 mM and changing LE+ concentration from 200 to 320 mM.

For the experiments demonstrating focusing and detection of 2,4,6-trichlorophenol (TCP), we used 150 mM Mes as LE−, 20 mM Hepes as TE−, 470 mM imidazole as LE+ and 300 mM Bistris as TE+. To increase the sample loading by continuously focusing the sample, we mixed TCP with TE−/LE+ mixture (diluted from 1 mM stock).

To visualize zones in all experiments, we prepared 1 mM stock solution of the Alexa Fluor 488 dye (Invitrogen, Carlsbad, Calif.) and used it as a fluorescent NFT by mixing at a concentration of 25 μM in the TE−/LE+ mixtures. We prepared 1 M stock solutions of Mops, Mes, Tricine, Hepes, Imidazole, Bistris and 200 mM solution of Taurine before diluting them to the desired concentrations in different solutions. We added 1% w/w polyvinylpyrrolidone (PVP) to all solutions to suppress electroosmotic flow (EOF). All chemicals were obtained by Sigma Aldrich (St. Louis, Mo.) and were prepared in UltraPure DNase/RNase-free distilled water (GIBCO Invitrogen, Carlsbad, Calif.).

We captured images using an inverted epifluorescent microscope (IX70, Olympus, Hauppauge, N.Y.) equipped with a LED lamp (LEDC1, Thor Labs, Newton, N.J.), U-MWIBA filter-cube from Olympus (460-490 nm excitation, 515 nm emission, and 505 nm cut off dichroic), and 2× (NA=0.08) and 10× (NA=0.3) objectives (Olympus). Images were captured using a 12 bit, 1300×1030 pixel array CCD camera (Micromax1300, Princeton Instruments, Trenton, N.J.). We controlled the camera using Winview32 (Princeton Instruments) and processed the images with MATLAB (R2007b, Mathworks, Natick, Mass.). We conducted the experiments by applying either constant voltage or current using a sourcemeter (model 2410, Keithley Instruments, Cleveland, Ohio).

All experiments were performed on off-the-shelf Caliper NS12A borosilicate glass microchips from Caliper Life Sciences (Mountain View, Calif.). All channels are isotropically etched to a depth of 20 μm with a mask width of 50 μm. Although the chip had four channels in a cross-geometry (e.g., as shown on FIG. 5a), we used only one channel (53 mm long) for our experiments. We filled the North, South and East reservoirs of the chip with LE−/LE+ mixture and applied vacuum to the West reservoirs until all channels were filled. We then rinsed the East and the West reservoirs with distilled water and filled them with cationic and anionic TE solutions, respectively.

B3) Results and Discussions

B3.1) Theory of Cascade ITP

In ITP, analytes focus between LE and TE zones under applied electric field only if their electrophoretic mobilities are less than that of LE ions in the LE zone and greater than TE ions in the TE zone. When present in large quantities, analytes in ITP focus and segregate into plateau-like zones, whose concentrations are directly proportional to the LE concentration. Thus, for a fixed amount of focused analyte, zone length ($\Delta_a$) is inversely proportional to the LE concentration ($c_L$). Furthermore, regardless of the injection scheme, the maximum amount of sample which can be focused (load capacity, $N_a$) is proportional to the LE concentration. For maximum attainable zone length in ITP, the effects of LE concentration on load capacity and the analyte zone concentration cancel since $$N_a \propto c_L, \Delta_a \propto \frac{N_a}{c_L}. \tag{3}$$

Therefore in ITP with uniform LE concentration, the maximum achievable zone length does not change with LE concentration. However, in cascade ITP, this limitation does not exist since load capacity is determined by the high concentration LE, while analyte zone concentration during detection is governed by the low concentration LE.

In cascade ITP, analytes first focus behind high concentration LE which allows for higher sample loading ($N_a \propto c_{L,high}$). The analyte zones are subsequently detected in a region following LE at low concentration, where the analyte zone concentrations are proportional to the lower LE concentration ($c_{L,low}$). The maximum zone length of focused analytes in cascade ITP, therefore, scales with the ratio of high to low LE concentrations, $$N_a \propto c_{L,high}, \Delta_a \propto \frac{N_a}{c_{L,low}}, \Delta_a \propto \frac{c_{L,high}}{c_{L,low}}. \tag{4}$$

Further, in cascade ITP, for a fixed amount of analyte focused between the LE and TE, the ratio of analyte zone length in the high and low concentration LE is given by, $\Delta_{a,after}/\Delta_{a,before} = c_{L,high}/c_{L,low}$. Here subscripts before and after denote the state of analyte zones in regions formerly occupied by high and low LE concentrations, respectively. Thus, the increase in zone length due to the transition of analyte zone is set simply by the concentrations of the two LEs.

B3.2) Prediction of Increase in Zone Length in Bidirectional ITP

Unlike conventional cascade ITP, the gradient in LE concentration in our technique (shown in FIGS. 7a-c) is generated in situ. Therefore, the increase in zone length in our technique is not known directly from the initial conditions. To study the effect of shock interaction on analyte zone lengths, we here develop a simplified model for bidirectional ITP with interacting shocks. Knowing the composition of initial LE−/LE+ mixture and the species mobilities, our model predicts the concentrations of analyte zones before and after the shock interaction. The change in analyte zone concentration due to shock interaction can then be related to the change in the zone lengths.

We begin by considering an electrolyte system consisting of N chemical species. We assume safe pH conditions (5<pH<9) and that all species are univalent acids or bases. We note these conditions are satisfied by the experiments presented in Sections B3.4-B3.6. For simplicity, we neglect the effect of ionic strength on electrophoretic mobilities of species (later in Section B3.3, we show detailed numerical simulations where we include the effects of ionic strength on species mobilities). Under these assumptions, we can relate species concentrations in different bidirectional ITP zones to the initial concentrations of LE− and LE+. For N species, the Jovin function, J(x,t), and the Alberty function, A(x,t), can be written as $$J(x, t) = \sum_{i=1}^{N} z_i c_i(x, t) = J(x, 0), \tag{5}$$

$$A(x, t) = \sum_{i=1}^{N} \frac{z_i c_i(x, t)}{\mu_i^0} = A(x, 0).$$

Here $z_i$, $c_i$ and $\mu_i^0$ respectively denote the valence, total (analytical) concentration, and absolute mobility of species i. Throughout, we use $c_i$ to denote the total concentrations of species i. That is, $c_i$ denotes the sum total of concentrations of all ionization states belonging to species I, including ionic and non-ionic states. Mobility is here defined as the ratio of actual drift velocity to local electric field, a signed quantity. The superscript 0 in mobility refers to the absolute mobility defined as the species mobility when fully ionized at zero ionic strength. Eliminating the concentration of $N^{th}$ species from the Jovin and Alberty functions defined in Eq. (5), we define a new conservation function, $$F(x, t) = \sum_{i=1}^{N-1} \left( \frac{1}{\mu_i^0} - \frac{1}{\mu_N^0} \right) z_i c_i(x, t) = F(x, 0). \tag{6}$$

We now use this combined Jovin-Alberty function, F(x,t), to determine concentrations of analyte zones before and after the shock interaction.

As shown in FIG. 7a, initially the channel is filled with the LE−/LE+ mixture 726, which alone sets the value of the combined Jovin-Alberty function throughout the channel. When electric field is applied, S− ions displace LE− ions and their concentration adjusts to the value of F(x,t) set by the LE−/LE+ mixture (FIG. 7b). Using LE+ as the $N^{th}$ species in Eq. (6), we obtain the concentration of focused analyte before the shock interaction ($c_{S-,before}$) in terms of the initial LE− concentration ($c_{L-,init}$), $$\left( \frac{1}{\mu_{S-}^0} - \frac{1}{\mu_{L+}^0} \right) c_{S-,before} = \left( \frac{1}{\mu_{L-}^0} - \frac{1}{\mu_{L+}^0} \right) c_{L-,init}. \tag{7}$$

Here, subscripts S−, L− and L+ denote analyte, LE− and LE+ ions, respectively. The second superscript init denotes the initial value. When the anionic and cationic ITP shocks interact, TE+ replaces LE+ as the counter-ion for anionic ITP (see FIG. 7c). To obtain the concentration of analyte after the shock interaction, $c_{S-,after}$, we now choose TE+ (denoted by T+) as the $N^{th}$ species in Eq. (6), $$\left(\frac{1}{\mu_{S-}^0} - \frac{1}{\mu_{T+}^0}\right) c_{S-,after} = \left(\frac{1}{\mu_{L-}^0} - \frac{1}{\mu_{T+}^0}\right) c_{L-,init} - \left(\frac{1}{\mu_{L+}^0} - \frac{1}{\mu_{T+}^0}\right) c_{L+,init}^0. \quad (8)$$

Equations (7) and (8) give the expressions for analyte zone concentrations before and after the shock interaction in terms of the species mobilities and the initial concentrations of LE+ ($c_{L+,init}$), and LE− ($c_{L-,init}$). For a fixed amount of accumulated sample, the gain in zone length due to shock interaction is, therefore, given by, $$\frac{\Delta_{after}}{\Delta_{before}} = \frac{c_{S-,before}}{c_{S-,after}} \quad (9)$$

$$= \left(\frac{1 - \mu_{L+}^0/\mu_{L-}^0}{1 - \mu_{L+}^0/\mu_{S-}^0}\right)\left(\frac{1 - \mu_{T+}^0/\mu_{S-}^0}{1 - \mu_{T+}^0/\mu_{L-}^0}\right)$$

$$\left[1 - \frac{c_{L+,init}}{c_{L-,init}}\left(\frac{1 - \mu_{T+}^0/\mu_{L+}^0}{1 - \mu_{T+}^0/\mu_{L-}^0}\right)\right]^{-1}.$$

The three parenthetic expressions in the above expression for $\Delta_{after}/\Delta_{before}$ are the ratios $c_{S-,before}/c_{L-,init}$, $c_{L-,after}/c_{S-,after}$, and $c_{L-,init}/c_{L-,after}$, respectively. In typical ITP experiments, the ratio of LE concentration to the corresponding analyte zone concentration is order unity. Therefore, the first two terms in Eq. (9) do not contribute, significantly, to the increase in zone length; and the expression for $\Delta_{after}/\Delta_{before}$ in Eq. (9) can be approximated as roughly as $$\frac{\Delta_{after}}{\Delta_{before}} \approx \left[1 - \frac{c_{L+,init}}{c_{L-,init}}\left(\frac{1 - \mu_{T+}^0/\mu_{L+}^0}{1 - \mu_{T+}^0/\mu_{L-}^0}\right)\right]^{-1}. \quad (10)$$

In other words, the change in zone length is primarily due to the ratio of LE− concentrations across the cationic ITP shock, and to a lesser extent due to the change in counter-ion from LE+ to TE+ upon shock interaction. Equation (10) is useful to quickly and approximately evaluate the effectiveness of electrolyte chemistry in increasing the detection sensitivity via shock interaction. For example, choosing $c_{L+,init}/c_{L-,init}=3$, $\mu_{T+}^0/\mu_{L+}^0=2/5$, and $\mu_{T+}^0/\mu_{L-}^0=-1$, by Eq. (10) yields up to 10 fold increase in the zone length due to shock interaction.

The analytical expression for increase in zone length given by Eq. (10) allows us to derive guidelines for choosing electrolyte chemistry to maximize the detection sensitivity. Firstly, the gain in zone length increases by increasing the proportion of LE+ in the initial LE−/LE+ mixture, i.e., higher $c_{L+,init}/c_{L-,init}$ ratio. Secondly, choosing TE+ as a weak base with a very low absolute mobility compared to that of LE+ (lower $\mu_{T+}^0/\mu_{L+}^0$ ratio) favors longer analyte zones after the shock interaction. When these two conditions are satisfied, the higher value of the total LE+ concentration in the LE+/LE− mixture causes TE+ to adjust to a high total concentration relative to the approximately fully ionized LE− concentration. That is, TE+ is then a weak base which is only partially ionized behind the LE+/TE+ interface at these conditions. As a result the conductivity of TE+ zone drops significantly and the local electric field correspondingly jumps to a significantly higher value behind the LE+/TE+ interface. Choosing TE+ with very low absolute mobility also promotes this by further lowering local conductivity behind the cationic ITP shock. The high local electric field in the TE+ zone is consistent with a strong decrease of LE− concentration, in accordance with the continuity of electromigration flux across the cationic ITP shock. As the shocks interact, the LE−/TE+ mixture with low LE− concentration replaces the initial LE−/LE+ mixture as the leading electrolyte for anionic ITP. This causes anionic ITP zones to readjust to lower LE concentrations and longer lengths. This achieves cascade ITP automatically and robustly with absolutely no actuation (such as voltage changes, electric switches, or valves).

We here provide some examples of viable electrolyte chemistries for our technique. These can be used to increase the sensitivity of anionic ITP by just modifying the initial electrolyte chemistries. The key requirements are that LE+ concentration should be high compared to LE− concentration, and TE+ ions should have very low absolute mobility compared to LE+ ions. Since the required concentrations of LE+ and TE+ in our method are higher than those of anionic species, we choose LE+ and TE+ as weak bases so as to keep the ITP zones well buffered. Several choices exist for high and low mobility weak bases applicable as LE+ and TE+, respectively. Table 2 shows three practical choices each for LE+ and TE+, combination of which yield nine unique initial chemistries. On the other hand, there are no specific constraints on LE− and TE− except the usual requirements on species mobilities for focusing anions in anionic ITP.

To obtain the analytical expression for increase in zone length (Eq. (9)) we have neglected the effect of ionic strength on species mobilities. However, ITP experiments are generally performed at higher ionic strengths (10-100 mM range) to achieve higher buffering capacity. Therefore the analytical model above is strictly only valid in the limit of zero ionic strength, and should be used only for qualitative analyte selections and rough predictions of the effect of electrolyte chemistry on the zone length. For more quantitative estimates of zone length, it is necessary to couple a model of ionic strength effects on species mobility with ITP dynamics.

Here we use the SPRESSO simulation tool to solve one-dimensional species transport equations coupled with Onsager-Fuoss and Debye-Huckel models for ionic strength dependence on mobilities and ionic activities, respectively. Time dependent simulations using SPRESSO are particularly useful for predicting transient behavior, such as analyte focusing during the startup and zone elongation due the shock interaction. However, for quicker estimates of increase in zone length in bidirectional ITP, we have also developed and used a steady solver based on a diffusion-free model of ITP. The solver computes species concentrations in all bidirectional ITP zones by solving the moving boundary equations (Hugoniot conditions across ITP shocks) coupled with models for the effect of ionic strength on mobilities and acid dissociation constants. We used both SPRESSO and this steady-state solver to design and analyze the processes described here. Unless otherwise stated, all simulations presented below are from SPRESSO.

TABLE 2

Possible cationic ITP buffer systems which are compatible with bidirectional, cascade ITP. These buffers effect large increase in zone lengths of anionic analytes upon shock interaction in bidirectional ITP. Listed are absolutely mobilities of the cations and their acid dissociation constant.

| | $\mu_{+1}$ (×$10^{-9}$ m$^2$V$^{-1}$s$^{-1}$) | pK$_{a,+1}$ |
|---|---|---|
| Cationic LE (LE+) | | |
| Imidazole | 52 | 7.15 |
| 2-methyl pyridine | 40.1 | 6.2 |
| 4-methyl pyridine | 40.1 | 6.1 |

TABLE 2-continued

Possible cationic ITP buffer systems which are compatible with bidirectional, cascade ITP. These buffers effect large increase in zone lengths of anionic analytes upon shock interaction in bidirectional ITP. Listed are absolutely mobilities of the cations and their acid dissociation constant.

| | $\mu_{+1}$ ($\times 10^{-9}$ $m^2V^{-1}s^{-1}$) | $pK_{a,+1}$ |
|---|---|---|
| Cationic TE (TE+) | | |
| Bistris | 26 | 6.4 |
| Pyridine | 30 | 5.18 |
| Tris | 29.5 | 8.07 |

B3.3) Simulation of Cascade ITP Process in Bidirectional ITP

We performed simulations of the bidirectional, cascade ITP process for focusing and separation of two model analytes in bidirectional ITP using the SPRESSO simulation tool. For our simulations, we used 100 mM Mops as LE−, 20 mM Taurine as TE−, 280 mM Imidazole as LE+, 100 mM Bistris as TE+, and Hepes (S1−) and Tricine (S2−) as the model analytes. To illustrate the technique, we used a finite injection scheme for our simulations where S1− and S2− were initially present between the LE− and TE− zones. Further, we chose our initial conditions such that the analytes focused completely in plateau mode prior to shock interaction. This allowed us to quantify, exactly, the increase in zone length due to shock interaction. All simulations shown here take into an account the effect of ionic strength on both mobilities and dissociation constants.

Figure 8A:
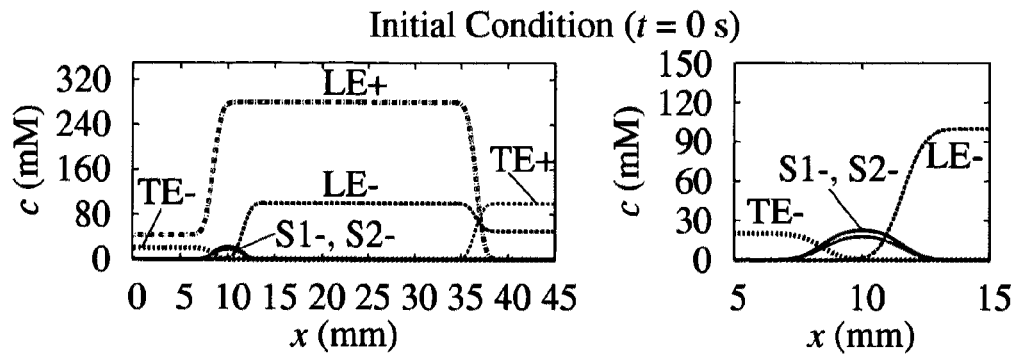
Figure 8B:
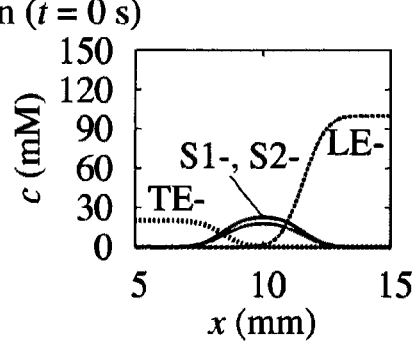
Figure 8C:
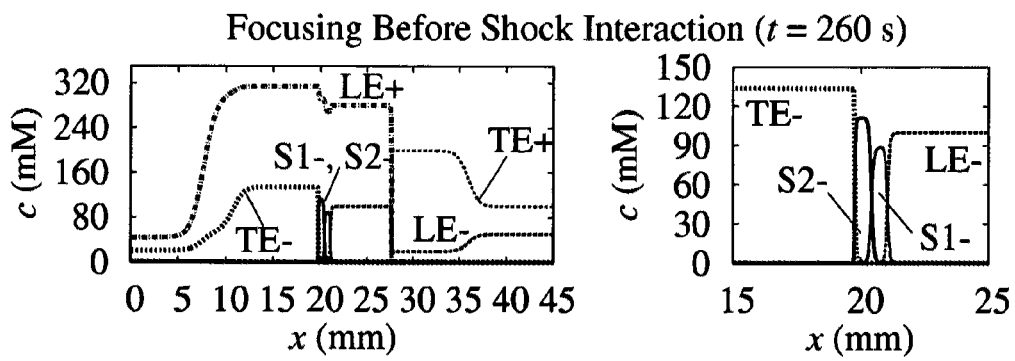
Figure 8D:
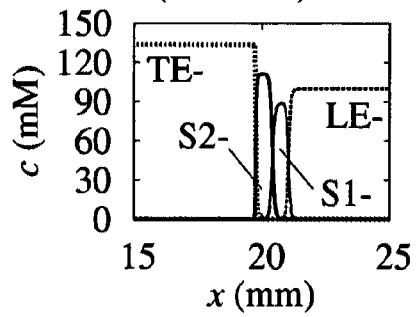

FIGS. 8a-h show simulation results showing an increase in zone length of anionic analytes using concentration cascade of LE− in bidirectional ITP. Plots in the second column are magnified views of species distributions shown in the first column. FIGS. 8a and 8b show the initial conditions of the simulation. Analytes S1− and S2− are placed between LE− and TE− zones. When electric field is applied, S1− and S2− focus and separate into distinct zones between LE− and TE−, as shown in FIGS. 8c and 8d. Simultaneously, a cationic ITP shock (LE+/TE+ interface) interface forms between the LE+ and TE+ zones and propagates leftward. Behind the LE+/TE+ interface, the concentration of LE− drops significantly compared to its initial concentration (FIG. 8c). By the time the LE+/TE+ interface meets the focused analytes, the high concentration LE− is completely replaced by the low concentration LE−. Because the analyte zone concentrations in ITP are proportional to the LE concentration, the interaction of cationic and anionic ITP shocks results in a decrease in zone concentrations of S1− and S2−. This readjustment of analyte zone concentrations is accompanied by simultaneous increase in their zone lengths. FIGS. 8e and 8f, show this transition from high to low concentration LE−, where the S1− zone has partially readjusted to the lower concentration and S2− is still focused at high concentration. FIGS. 8g and 8h show the final state where both S1− and S2− are fully adjusted to new concentrations, and their zone lengths have increased (5-fold in this case) compared to those before the shock interaction. Also, the cationic ITP shock remains intact after the shock interaction and continues propagating leftwards. We assumed a constant current of 2 µA, and a D-shaped, wet-etched channel 90 µm wide and 20 µm deep. We approximately account for electroosmotic flow assuming variation of local electroosmotic mobility as $\mu = \mu_r(\sigma_r/\sigma)^{1/3}$, where $\mu_r = 3 \times 10^{-10}$ $V^{-1} \cdot m^2 \cdot s^{-1}$ and $\sigma_r = 0.5$ $S \cdot m^{-1}$.

The simulation of cascade ITP process in bidirectional ITP as shown in FIGS. 8a-h highlights several advantages of our technique over conventional cascade ITP. As shown in FIG. 8c, the gradient in LE− concentration forms inside the channel by simply applying an electric field. Our technique, therefore, eliminates integration of two or more channels containing different concentrations of LE− via valves or column coupling arrangements, as done in conventional cascade ITP. This in situ generation of cascade in LE concentration makes it possible to perform cascade ITP in a single channel, so it is easily accomplished in on- or off-chip systems. Further, in the current technique, the gradient in LE concentration remains sharp over time as it sweeps across the focused analyte zones. This is in contrast to conventional cascade ITP, where the interface between high and low concentration LE diffuses over time and is susceptible to dispersive effects of non-uniform electroosmotic flow and hydrodynamic flow. This well controlled, sharp gradient in LE concentration provides us with a fast transition from focusing at high concentration LE to low concentration LE. In contrast, a complete readjustment of analyte zones to lower concentration LE is not achieved in traditional cascade ITP until the analyte zones completely migrate out of the diffused region between the high and low concentration LE. This feature of our assay minimizes required channel lengths and assay time.

We also performed a simulation at conditions which allow experimental visualization of all bidirectional ITP zones. For this, we used the same electrolyte chemistry as in the simulation shown in FIGS. 8a-h. In addition to that, we simulated mixing of a fluorescent non-focusing tracer (NFT) into the initial TE−/TE+ mixture. This NFT was faster than all other anions. The NFT is in trace concentration so it does not focus or disturb zone concentrations in bidirectional ITP, but its concentration quickly adapts to all local electric fields. The NFT fluorescent intensity distribution therefore clearly delineates the various bidirectional ITP zones. In Section B3.4 we present corresponding experimental validation of this simulation and discuss the NFT visualization technique in more detail.

Figure 9A:
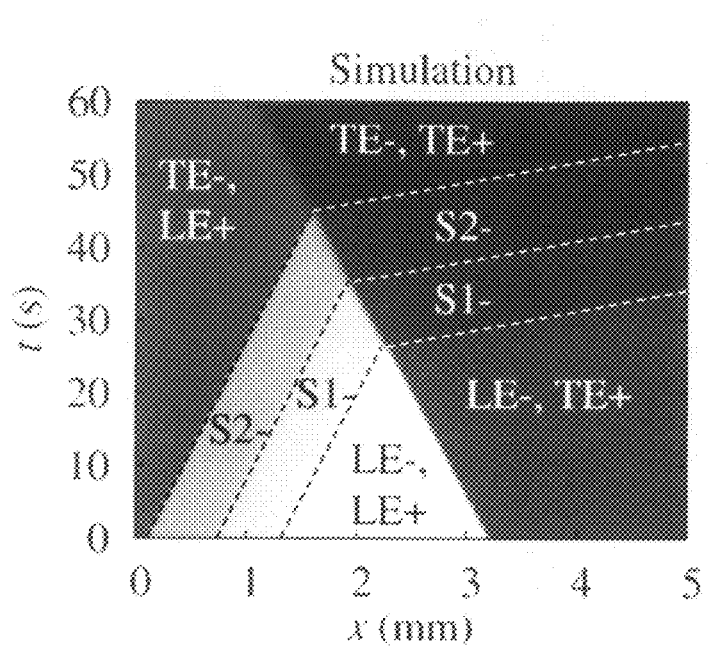
FIGS. 9a-b show a comparison between simulated and experimental results for the focusing to focusing mode.
Figure 9B:
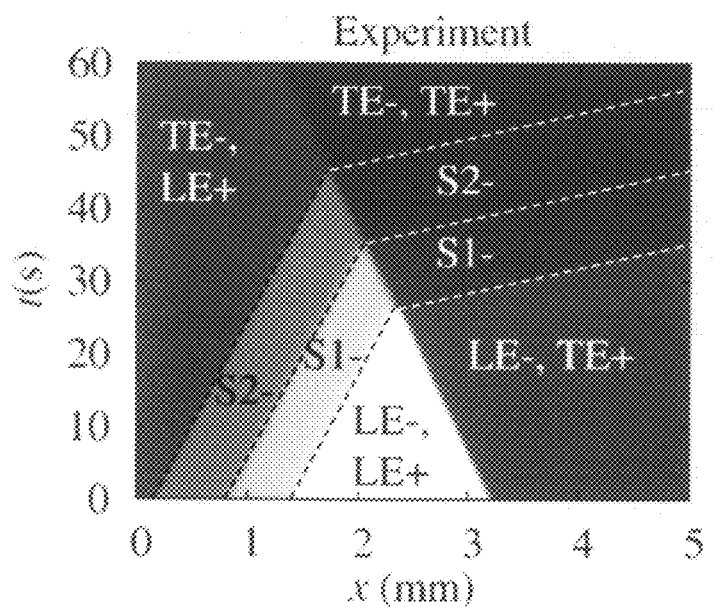

FIGS. 9a-b show numerical simulation and experimental visualization of increase in analyte zone length due to interaction of anionic and cationic ITP shocks. FIG. 9a shows numerical simulation of propagating zones of anionic analytes (S1− and S2−) and a cationic ITP shock in bidirectional ITP. The spatiotemporal plot shows the intensity of a fluorescent non-focusing tracer (NFT) versus the distance along the channel axis, x, and time, t. Here, the abscissa is the distance along the channel, the ordinate is time, and the scalar plotted is the fluorescent intensity of the NFT. To obtain the spatiotemporal plot from simulation, we neglect the effects of photobleaching and assumed a proportional relationship between the fluorescent intensity and the NFT concentration. The NFT does not focus via ITP, but its concentration adapts to the local electric field in each zone. Regions of different fluorescence intensity mark ITP zones. FIG. 9b shows experimental visualization of the same process using the fluorescent non-focusing tracer (NFT) technique. Dashed lines have been added to FIGS. 9a-b to emphasize interfaces between the various zones.

FIGS. 9a-b both show anionic analyte zones and LE+/TE+ interface (cationic ITP shock) propagating towards the right and left, respectively. The LE+/TE+ interface meets the focused analyte zones near x=2.3 mm and t=25 s. Thereafter the analyte zones elongate five-fold and the LE+/TE+ interface continues migrating leftward (for t>25 s). The elongation of analyte zones around t=25 s, is accompanied by an increase in their migration speed (visible as a decrease in slope of anionic ITP shocks). The electrolyte chemistry and electroosmotic mobility is the same as that in the simulation shown in FIGS. 8a-h, except that in this case we mixed 25 µM Alexa Fluor 488 (NFT) in TE− to visualize ITP zones. We assumed a constant current of 2 µA, and a 53 mm long D-shaped, wet-etched channel 90 µm wide and 20 µm deep.

Since the NFT and LE− are both counter-ions for cationic ITP, their concentrations across the LE+/TE+ interface are proportional to each other. The low fluorescent intensity in the LE−/TE+ zone compared to the LE−/LE+ zone, therefore, indirectly quantifies the manifold decrease in LE− concentration across the LE+/TE+ interface. When the anionic and cationic ITP shocks interact, the analyte zones readjust to lower concentrations (shown by the decrease in NFT intensity in the analyte zones) and achieve longer zone lengths. After the LE+/TE+ interface completely passes over the analyte zones, the zone lengths reach steady state values that are much greater than those before the shock interaction. To take into an account the effect of electroomostic flow on the wave speeds in our simulations, we used the following approximate electroosmotic mobility dependence on conductivity: $\mu = \mu_r (\sigma_r/\sigma)^{1/3}$, where $\mu_r = 3 \times 10^{-10} V^{-1} m^2 s^{-1}$ and $\sigma_r = 0.5 Sm^{-1}$. The product $\mu_r \sigma_r^{1/3}$ is therefore the only fitting parameter used to match all experimentally measured shock speeds. (See Section B3.4 on experimental visualization of cascade ITP process in bidirectional ITP.)

B3.4) Experimental Visualization of Increase in Analyte Zone Length in Bidirectional ITP We performed visualization experiments to study the dynamics of cascade ITP in bidirectional ITP. For these experiments, we focused finite amount of analytes in anionic ITP and visualized the effect on their zone lengths during interaction with cationic ITP shock. We visualized the increase in zone lengths of focused analytes due to shock interaction in bidirectional ITP using the NFT technique. In the NFT technique, fluorescent species which do not obey the ITP focusing conditions are mixed with the ITP buffers in trace quantities. These fluorescent species do not focus in ITP, but their concentrations adapt to the local electric field and conductivity in different ITP zones. The fluorescent intensity of NFT, therefore, indicates the gradients in local conductivity across the ITP interfaces. For our experiments, we used 25 µM Alexa Fluor 488 (AF, an anionic dye) in the TE−/LE+ mixture as the NFT. In our experiments, AF is faster than all other anions and so does not focus in anionic ITP. Further, AF being an anionic species does not focus in cationic ITP. Hence, we visualized both anionic and cationic ITP zones in bidirectional ITP using AF as the lone NFT. We note that for cationic ITP, the concentration of anionic NFT is proportional to the concentration of background counter-ion. Therefore, in our experiments the gradient in NFT concentration across the cationic ITP shock indirectly quantifies the cascade in LE− concentration.

FIG. 9b shows an experimentally measured spatiotemporal plot of the fluorescent intensity of NFT in bidirectional ITP with a concentration cascade of LE−. In the plot, the abscissa is the distance along the channel axis, the ordinate is time, and the plotted scalar is the fluorescent intensity of NFT. Sharp interfaces separating zones of different intensity are the ITP shocks, and the slope of these interfaces are the inverse of ITP shock speeds. The plot shows zones of focused S1− and S2− propagating towards the right and a cationic ITP shock propagating towards the left. Sharp decrease in NFT intensity across the LE+/TE+ shock, prior to the shock interaction (t<25 s), indirectly indicates the cascade in LE− concentration. Before the shock interaction, analytes focus behind high concentration LE−. Between t=25 s and 45 s, the cationic ITP shock interacts with the focused analyte zones. During this transition, the analyte zone concentrations decrease and the zone lengths increase. The decrease in analyte zone concentrations is visible from the decrease in NFT intensity across the cationic ITP shock for 25 s<t<45 s. After the interaction of anionic analyte zones with the cationic ITP shock ends (t> 45 s), the analyte zone lengths reach a steady state and are about five times longer than the corresponding zone lengths before the shock interaction. Also, the cationic ITP interface remains intact after the interaction and continues propagating towards the left.

Our experimental visualizations compare well with the numerical simulations shown in FIG. 9a. Our simulations correctly predict the increase in lengths of analyte zones upon their interaction with the cationic ITP shock. Further, our simulations correctly predict the relative change in fluorescent intensity of NFT across ITP shocks. In our simulations, by using conductivity dependent electroosmotic mobility as the only fitting function, we correctly predict the time and the location of shock interactions and the eight observable shock speeds. We emphasize that for a fixed amount of sample, the zone lengths are independent of EOF and therefore by excluding EOF from our simulations we can still predict the zone lengths correctly.

B3.5) Effect of Electrolyte Chemistry on Increase in Zone Length

We performed experiments to validate the dependence of analyte zone lengths on the electrolyte chemistry as given by the analytical model in Section B3.2. According to the analytical model, for a given electrolyte chemistry, the increase in analyte zone length depends primarily on the ratio of LE+ to LE− concentrations in the initial LE+/LE− mixture. For our experiments, we therefore kept the same LE−/LE+ chemistry but used seven different ratios of LE+ to LE− concentrations ($c_{L+,init}/c_{L-,init}$) ranging from 2.0 to 3.2. The changes in composition of LE−/LE+ mixture were obtained by fixing the concentration of LE− at 100 mM and varying LE+ concentration from 200 mM to 320 mM. FIGS. 10a,c show the relative increase in zone length ($\Delta_{after}/\Delta_{before}$) of two analytes (Hepes and Tricine) due to shock interaction, for different proportions of LE+ in the LE−/LE+ mixture. The insets (FIGS. 10b,d) show the same data, but here the ordinate is the inverse of the gain in zone length, i.e. $\Delta_{before}/\Delta_{after}$. Our experiments show linear decrease in $\Delta_{before}/\Delta_{after}$ with increasing $c_{L+,init}/c_{L-,init}$, as predicted by the analytical model. Thus, the gain in zone length in our bidirectional ITP experiments increases non-linearly with increase in $c_{L+,init}/c_{L-,init}$.

More specifically, FIGS. 10a-d show the effect of the leading electrolyte composition on gain in analyte zone lengths due to shock interaction. FIGS. 10a,c show the variation of measured and theoretical gain in zone length ($\Delta_{after}/\Delta_{before}$) of two analytes (Hepes and Tricine) versus the ratio of LE+ to LE− concentration in the initial LE+/LE− mixture ($c_{L+}^0/c_{L-}^0$). The gain in analyte zone length increases non-linearly with increase in $c_{L+}^0/c_{L-}^0$. Both FIGS. 10a,c show theoretical predictions with and without ionic strength correction for species mobility. Theoretical predictions which take into an account the effect of ionic strength on mobilities are in good agreement with experimental observations. Theoretical predictions from the analytical model (without ionic strength corrections) under predict the gain in zone length. The insets (i.e., FIGS. 10b,d) show the comparison with same data, but now the ordinate is the inverse of the gain in zone length ($\Delta_{before}/c_{after}$) due to the shock interaction. Although the predictions using the analytical model do not agree well with the observed gain in zone length, the simple analytical solution correctly predicts the linear variation of $\Delta_{before}/c_{after}$ with $c_{L+}^0/\Delta_{L-}^0$. For these experiments, LE– is Mops, LE+ is Imidazole, TE– is 20 mM Taurine and TE+ is 100 mM Bistris. To vary the ratio $c_{L+}^0/c_{L-}^0$ we fixed the concentration of LE– at 100 mM and varied the concentration of LE+ from 200 mM to 320 mM. We visualized different ITP zones using the fluorescent NFT technique. For these experiments, we used Alexa Fluor 488 as the NFT. All theoretical results use the same conditions.

Our experimental results are in qualitative agreement with the analytical model, which correctly predicts the dependence of analyte zone length on the composition of LE–/LE+ mixture (FIGS. 10a-d). However, there is a discrepancy between the experimentally observed and analytically predicted gain in zone lengths. As shown in FIGS. 10a,c, the error in prediction by the analytical model increases for larger increase in zone lengths (at higher $c_{L+,init}/c_{L-,init}$). This error is attributed to neglect of the dependence of ionic strength on species mobilities in our analytical model. At high ionic strengths (around 100 mM) in our experiments the electrophoretic mobilities reduce considerably from the corresponding values of absolute mobilities. The analytical expression for the gain in zone length (given by Eqs. (9)) being a function of species mobilities, therefore, does not agree well with the experimental results.

In FIGS. 10a-d we also plot the gain in zone length calculated using the diffusion-free model with ionic strength correction for mobilities. The predictions using the diffusion-free model agree well with experimentally observed increase in zone length due to shock interaction. We note that simulations using SPRESSO can be used to correctly predict the zone lengths in bidirectional ITP, albeit at the expense of longer computational time. In FIGS. 10a-d, we omit the results from SPRESSO simulations, because the differences between the predicted values of zone lengths using the diffusion-free model and SPRESSO are negligible.

B3.6) Demonstration of High Sensitivity Detection Using Bidirectional ITP

Figure 11A:
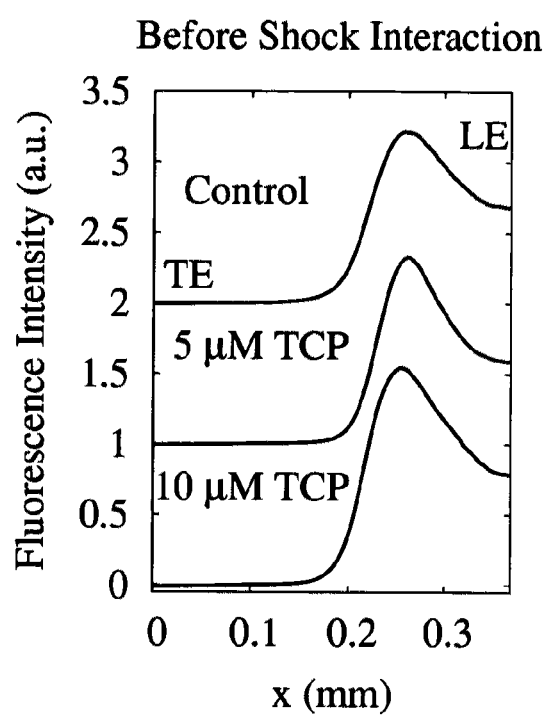
FIGS. 11a-b show experimental results relating to increased sensitivity provided by the focusing to focusing mode.
Figure 11B:
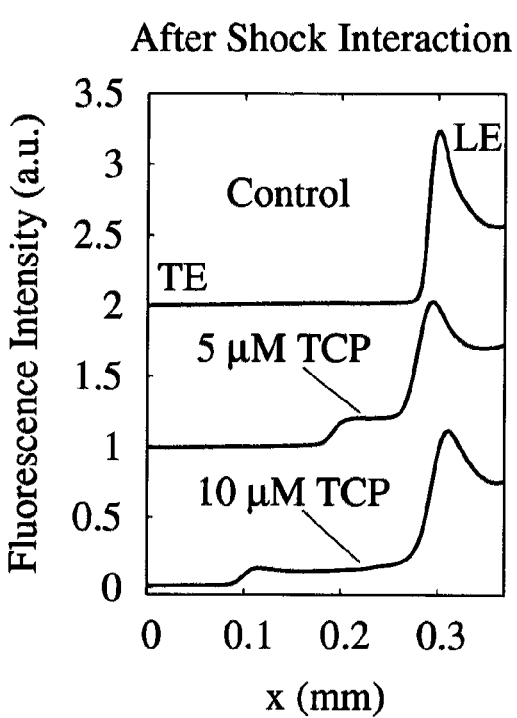

Lastly, we used bidirectional ITP with concentration cascade of LE– for high sensitivity detection of 2,4,6-trichlorophenol (TCP), which is a carcinogenic pollutant. The NFT technique using Alexa Fluor 488 as the NFT was employed. For these experiments we used 150 mM Mes as LE–, 20 mM Hepes as TE–, 470 mM Imidazole as LE+ and 300 mM Bistris as TE+. Our simulations predict ~20-fold increase in zone length due to shock interaction with this electrolyte chemistry. To increase the sample loading, we performed semi-infinite injection of TCP by mixing it with anionic TE (TE–/TE+ mixture). FIGS. 11a and 11b show isotachopherograms obtained before and after the shock interaction. For the control experiment, where no TCP was present in the TE–/LE+ mixture, we observe a single step in the NFT signal corresponding to the LE–/TE– interface. When TCP is spiked in anionic TE at concentrations of 5 μM and 10 μM, the signal before the shock interaction does not change. This is because TCP is focused in peak mode and, therefore, its zone length is of the order of LE–/TE– interface thickness. However, in the same experiments with 5 μM and 10 μM TCP mixed in TE– the TCP zone length increases upon its interaction with the cationic ITP shock. FIG. 11b shows well resolved plateau-like zones of TCP after the shock interaction. As expected, the TCP zone lengths are proportional to the initial amount of TCP in the anionic TE. Thus TCP which focuses in peak mode before the shock interaction transitions to plateau mode after the interaction of anionic and cationic ITP shock waves.

In these experiments we observe a signal overshoot at the boundary of LE– zone. Similar signal overshoots have been reported previously for NFT visualizations. However, we note that these overshoots do not affect our ability to detect and quantify the length of plateau-like zone of TCP. The detection sensitivity of our technique is currently in the μM range. The sensitivity can be further increased by at least a factor of 50 by using techniques such as cross-section variation and hydrodynamic counterflow. For these experiments, we used a constant potential of 500 V across a 53 mm long, D-shaped, wet-etched channel 90 μm wide and 20 μm deep.

The invention claimed is:

1. A method comprising:
    establishing anionic isotachophoresis (ITP) having one or more anionic ITP shock waves between an anionic leading electrolyte ion (LE–) and an anionic trailing electrolyte ion (TE–) in a channel;
    establishing cationic isotachophoresis having one or more cationic ITP shock waves between a cationic leading ion (LE+) and a cationic trailing ion (TE+) in the channel;
    selecting ions of the anionic ITP and the cationic ITP such that an interaction of the anionic ITP shock waves and cationic ITP shock waves modifies the effective mobility of one or more ions to provide a focusing-to-separation operation mode;
    wherein the anionic ITP shock waves and the cationic ITP shock waves propagate toward each other and interact when they meet;
    wherein one or more interaction regions are created by shock wave interaction of one or more of the anionic ITP shock waves with one or more of the cationic ITP shock waves; and
    analyzing at least one of the interaction regions to determine physicochemical properties of ions and/or interaction regions in the channel;
    further comprising isotachophoretic focusing of one or more analytes in a selected shock wave of the anionic and cationic ITP shock waves prior to the shock wave interaction; and
    further comprising electrophoretic separation of the one or more analytes in at least one of the interaction regions after the shock wave interaction, wherein shock wave interaction causes an automatic transition from an ITP focusing mode to an electrophoretic separation mode.

2. A method comprising:
    establishing anionic isotachophoresis (ITP) having one or more anionic ITP shock waves between an anionic leading electrolyte ion (LE–) and an anionic trailing electrolyte ion (TE–) in a channel;
    establishing cationic isotachophoresis having one or more cationic ITP shock waves between a cationic leading ion (LE+) and a cationic trailing ion (TE+) in the channel;
    selecting ions of the anionic ITP and the cationic ITP such that an interaction of the anionic ITP shock waves and cationic ITP shock waves modifies the effective mobility of one or more ions to provide a focusing-to-focusing operation mode;
    wherein the anionic ITP shock waves and the cationic ITP shock waves propagate toward each other and interact when they meet;
    wherein one or more interaction regions are created by shock wave interaction of one or more of the anionic ITP shock waves with one or more of the cationic ITP shock waves; and
    analyzing at least one of the interaction regions to determine physicochemical properties of ions and/or interaction regions in the channel;

further comprising isotachophoretic focusing of one or more analytes in a selected shock wave of the anionic and cationic ITP shock waves prior to the shock wave interaction; and further comprising isotachophoretic focusing of the one or more analytes in at least one of the interaction regions after the shock wave interaction, wherein shock wave interaction causes an automatic transition from an ITP focusing mode to another ITP focusing mode.

3. The method of claim 2, further comprising performing the method of claim 2 such that ITP zone lengths of analytes in at least one of the interaction regions differ from ITP zone lengths of the analytes prior to the shock wave interaction.

4. The method of claim 3, further comprising performing the method of claim 3 such that ITP zone lengths of analytes in at least one of the interaction regions are greater than ITP zone lengths of the analytes prior to the shock wave interaction.

5. The method of claim 1, further comprising performing the method of claim 1 such that the anionic ITP has two or more anionic ITP zones prior to the shock wave interaction, such that the cationic ITP has two or more cationic ITP zones prior to the shock wave interaction, and such that at least one of the interaction regions has a composition that is distinct from compositions of the anionic and cationic ITP zones.

6. The method of claim 1, further comprising extracting one or more of the interaction regions from the channel for use and/or further analysis.

7. The method of claim 1, wherein the physicochemical properties include one or more properties selected from the group consisting of: conductivity, ionic strength, ionization state, species identity, pH, absorption spectra, emission spectra, temperature, concentration, effective mobility, and electrophoretic mobility.

8. A method for purification and/or separation of analytes comprising:

performing the method of claim 1 on a sample including analytes.

9. The method of claim 8, wherein the analytes comprise one or more analytes selected from the group consisting of: DNA, DNA fragments, RNA, RNA fragments, proteins, protein fragments, polypeptides and amino acids.

10. The method of claim 9, wherein selective isotachophoretic focusing of a selected group of the analytes occurs in a shock wave of the anionic and cationic ITP shock waves.

11. The method of claim 10, wherein the analytes include one or more species of interest and one or more contaminant species, and wherein the selected group of the analytes includes the one or more species of interest and does not include the one or more contaminant species.

12. The method of claim 11, wherein the one or more species of interest include DNA species, and wherein the one or more contaminant species include proteins.

\* \* \* \* \*